(12) United States Patent
Deppert et al.

(10) Patent No.: US 7,910,704 B2
(45) Date of Patent: Mar. 22, 2011

(54) HUMAN P53 SPLICE VARIANT DISPLAYING DIFFERENTIAL TRANSCRIPTIONAL ACTIVITY

(76) Inventors: Wolfgang W. Deppert, Hamburg (DE); Irene Dornreiter, Hamburg (DE)

( * ) Notice: Subject to any disclaimer, the term of this patent is extended or adjusted under 35 U.S.C. 154(b) by 310 days.

(21) Appl. No.: 11/236,014

(22) Filed: Sep. 27, 2005

(65) Prior Publication Data

US 2006/0062792 A1    Mar. 23, 2006

Related U.S. Application Data

(63) Continuation-in-part of application No. PCT/EP2004/003299, filed on Mar. 29, 2004.

(30) Foreign Application Priority Data

Mar. 27, 2003    (EP) .................................... 03007000

(51) Int. Cl.
   C07K 14/00    (2006.01)
   C07K 16/00    (2006.01)
   C07K 17/00    (2006.01)
   C12P 21/08    (2006.01)
   A61K 38/16    (2006.01)

(52) U.S. Cl. ................ 530/387.9; 530/350; 530/380; 530/386; 530/387.1; 530/387.7; 530/388.1; 530/388.15

(58) Field of Classification Search .............. 530/350, 530/380, 386, 387.1, 387.7, 387.9, 388.1, 530/388.15
See application file for complete search history.

(56) References Cited

U.S. PATENT DOCUMENTS 6,307,036 B1    10/2001    Milner et al.

FOREIGN PATENT DOCUMENTS

WO    WO 00/22127    4/2000

OTHER PUBLICATIONS

Harlow and Lane. Antibodies, A Laboratory Manual, pp. 319-325 and 340-352, 1988.*
Gannon et al. Activating mutations in p53 produce a common conformational effect. A monoclonal antibody specific for the mutant form. The EMBO Journal 9(5): 1595-1602, 1990.*
Campomenosi, Paola, et al. p53 mutants can often transactivate promoters containing a p21 but not Bax or PIG3 responsive elements, *Oncogene* (2001) 20, pp. 3573-3579.
Dell' Acqua, G., et al. *p35: identification, characterization and functional studies of a novel p53 alternative splice product in the rat*, Brigham and Women's Hospital, Harvard Medical School (1999) p. 852.
El-Deiry, W.S. The p53 pathway and cancer therapy, *The Cancer Journal* (1998) 11, No. 5, pp. 229-236.
Fukuda I., et al., Alternatively-Spliced p53 mRNA in the FAA-HTC1 Rat Hepatoma Cell Line without the Splice Site Mutations, *Cell Structure and Fusion* (1992) 17, pp. 427-432.
Hermeking, Heiko, et al. 14-3-3σ Is a p53-Regulated Inhibitor of G2/M Progression, *Molecular Cell* (1997) 1, pp. 3-11.
Nakai, Hiroyuki, et al. Multiple aberrant splicing of the p53 transcript without genomic mutations around exon-intron junctions in a case of chronic myelogenous leukaemia in blast crisis: a possible novel mechanism of p53 inactivation, *British Journal of Haematology* (1994) 87, pp. 839-842.
Ruggeri, Bruce A., et al. Molecular Pathology of Primary and Metastatic Ductal Pancreatic Lesions, *American Cancer Society* (1997) 79, No. 4, pp. 700-716.

* cited by examiner

*Primary Examiner* — Alana M. Harris
(74) *Attorney, Agent, or Firm* — Lerner, David, Littenberg, Krumholz & Mentlik, LLP

(57) ABSTRACT

Novel human p53 splice variant displaying differential transcriptional activity Described is a nucleic acid molecule encoding a p53 variant characterized in that it is capable of transactivating the p21- and 14-3-3σ-promoter but not the mdm2-, bax- and PIG3-promoter. Preferably, in said p53 variant exon 7, exon 8 and/or exon 9 are partially or entirely deleted. Finally, means for inhibiting the activity of this p53 variant are described which are useful for the therapy of cancer.

9 Claims, 14 Drawing Sheets

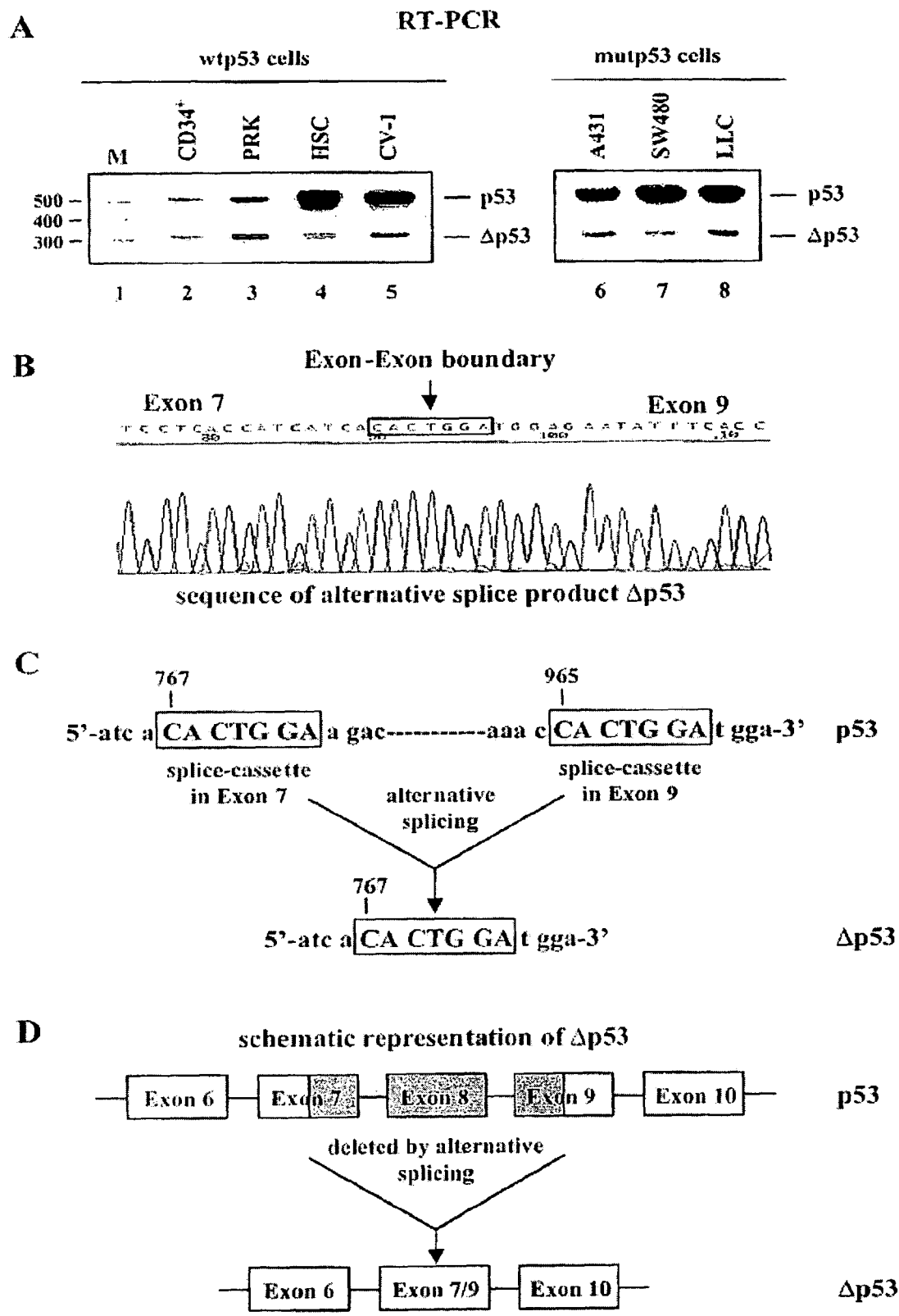
Figure 1 (A, B, C and D)

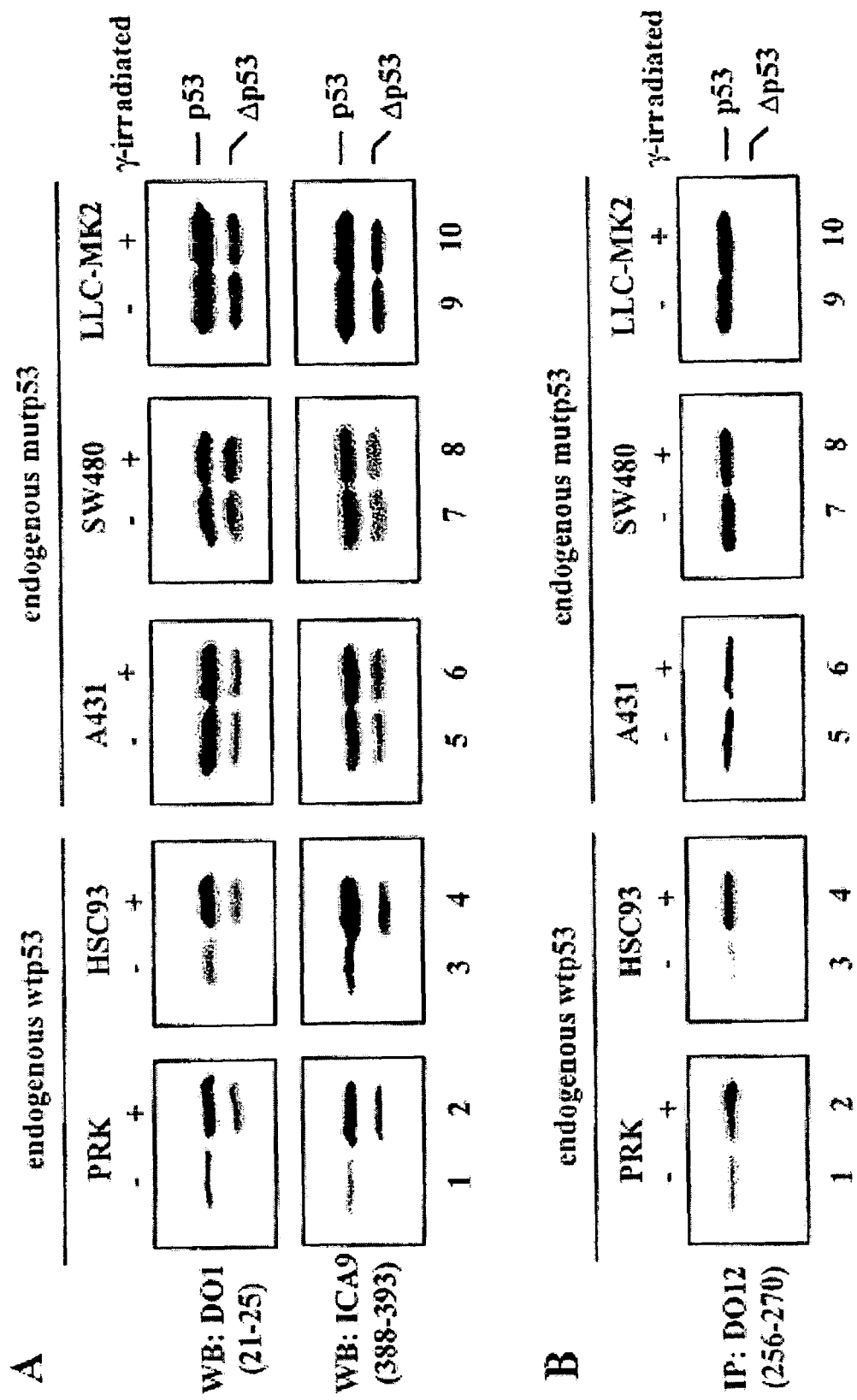
Figure 2 (A and B)

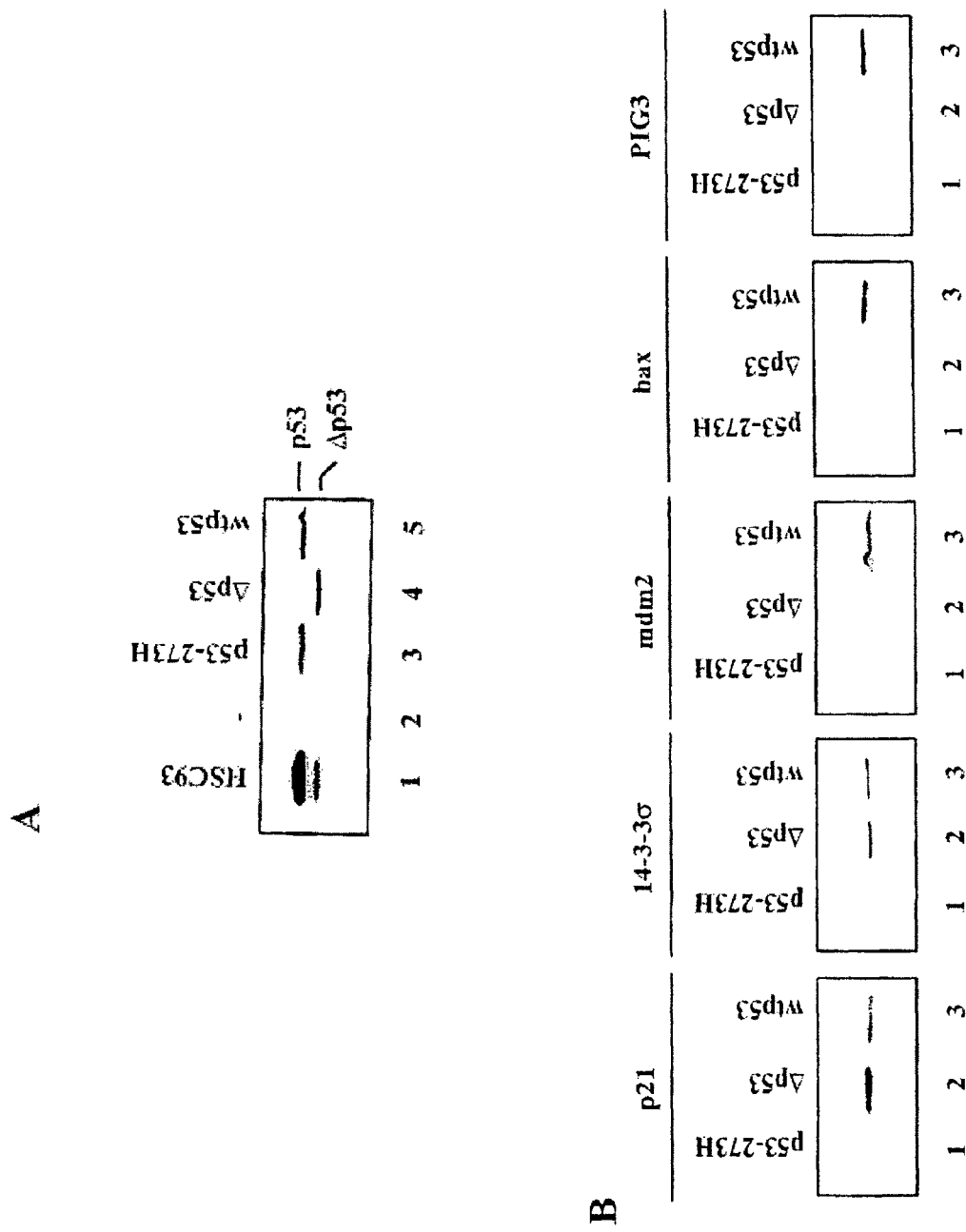
Figure 3 (A and B)

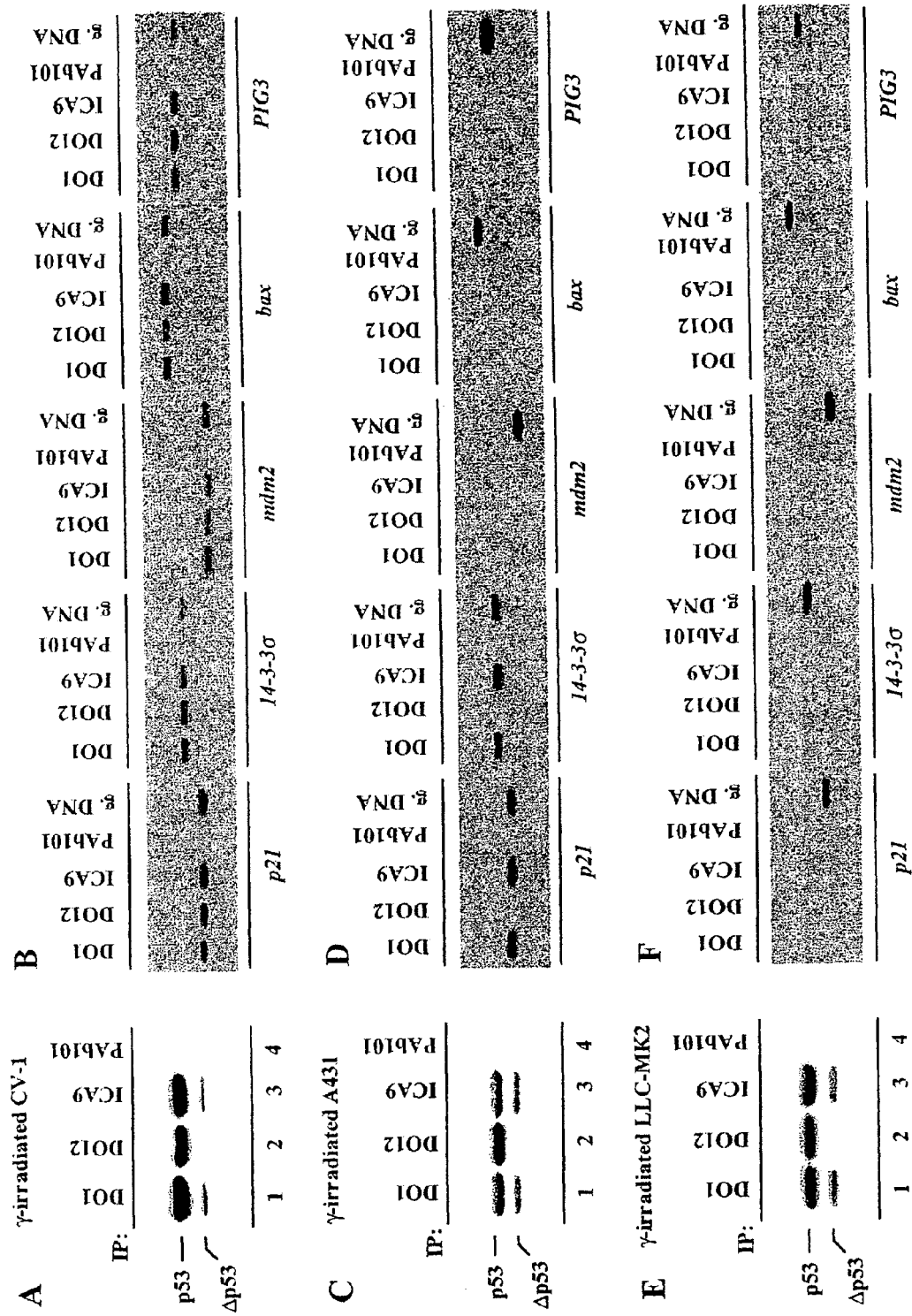
Figure 4 (A, B, C, D, E and F)

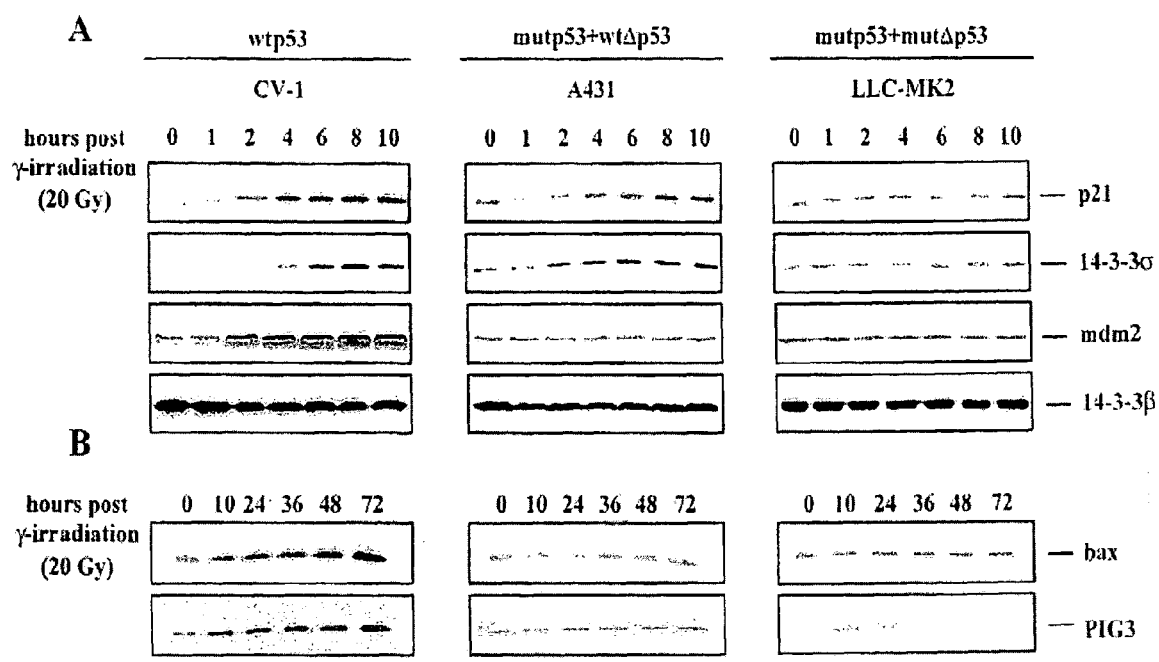
Figure 5 (A and B)

A

A

MEEPQSDPSVEPPLSQETFSDLWKLLPENNVLSPLPSQAMDDLMLSPDDIEQWFTE
DPGPDEAPRMPEAAPRVAPAPAAPTPAAPAPAPSWPLSSSVPSQKTYQGSYGFRL
GFLHSGTAKSVTCTYSPALNKMFCQLAKTCPVQLWVDSTPPPGTRVRAMAIYKQSQ
HMTEVVRRCPHHERCSDSDGLAPPQHLIRVEGNLRVEYLDDRNTFRHSVVVPYEPPE
VGSDCTTIHYNYMCNSSCMGGMNRRPILTIITLDGEYFTLQIRGRERFEMFRELNEALE
LKDAQAGKEPGGSRAHSSHLKSKKGQSTSRHKKLMFKTEGPDSD

B p53   meepqsdpsv epplsqetfs dlwkllpenn vlsplpsqam ddlmlspddi eqwftedpgp

Δp53 meepqsdpsv epplsqetfs dlwkllpenn vlsplpsqam ddlmlspddi eqwftedpgp p53   deaprmpeaa prvapapaap tpaapapaps wplsssvpsq ktyqgsygfr lgflhsgtak Δp53 deaprmpeaa prvapapaap tpaapapaps wplsssvpsq ktyqgsygfr lgflhsgtak p53   svtctyspal nkmfcqlakt cpvqlwvdst pppgtrvram aiykqsqhmt evvrrcphhe Δp53 svtctyspal nkmfcqlakt cpvqlwvdst pppgtrvram aiykqsqhmt evvrrcphhe p53   rcsdsdglap pqhlirvegn lrveylddrn tfrhsvvvpy eppevgsdct tihynymcns Δp53 rcsdsdglap pqhlirvegn lrveylddrn tfrhsvvvpy eppevgsdct tihynymcns p53   scmggmnrrp iltiitleds sgnllgrnsf evrvcacpgr drrteeenlr kkgephhelp Δp53 scmggmnrrp iltiit................................................

p53   pgstkralpn ntssspqpkk kp ldgeyftl qirgrerfem frelnealel kdaqagkepg

Δp53 ........................ldgeyftl qirgrerfem frelnealel kdaqagkepg p53   gsrahsshlk skkgqstsrh kklmfktegp dsd Δp53 gsrahsshlk skkgqstsrh kklmfktegp dsd

Figure 7 (A and B)

```
atggaggagc cgcagtcaga tcctagcgtc gagcccctc tgagtcagga aacatttca     60
gacctatgga aactacttcc tgaaaacaac gttctgtccc ccttgccgtc ccaagcaatg   120
gatgatttga tgctgtcccc ggacgatatt gaacaatggt tcactgaaga cccaggtcca   180
gatgaagctc ccagaatgcc agaggctgct cccccgtgg cccctgcacc agcagctcct   240
acaccggcgg cccctgcacc agccccctcc tggcccctgt catcttctgt cccttcccag   300
aaaacctacc agggcagcta cggtttccgt ctgggcttct tgcattctgg gacagccaag   360
tctgtgactt gcacgtactc ccctgcccctc aacaagatgt tttgcaaact ggccaagacc   420
tgccctgtgc agctgtgggt tgattccaca cccccgccg gaggttgtga ggcgctgccc   480
gccatctaca agcagtcaca gcacatgacg gaggttgtga ggcgctgccc caccatgag   540
cgctgctcag atagcgatgg tctggccct cctcagcatc ttatccgagt ggaaggaaat   600
ttgcgtgtgg agtatttgga tgacagaaac acttttcgac atagtgtggt ggtgccctat   660
gagccgcctg aggttggctc tgactgtacc accatccact acaactacat gtgtaacagt   720
tcctgcatgg gcggcatgaa ccggaggccc atcctcacca tcatcacact ggatggagaa   780
tatttcacc ttcagatccg tgggcgtgag cgcttcgaga tgttccgaga gctgaatgag   840
gccttggaac tcaaggatgc ccaggctggg aaggagccag gggagcag ggctcactcc   900
agccacctga agtccaaaaa gggtcagtct acctcccgcc ataaaaaact catgttcaag   960
acagaagggc ctgactcaga ctga                                          984
```

Figure 7C

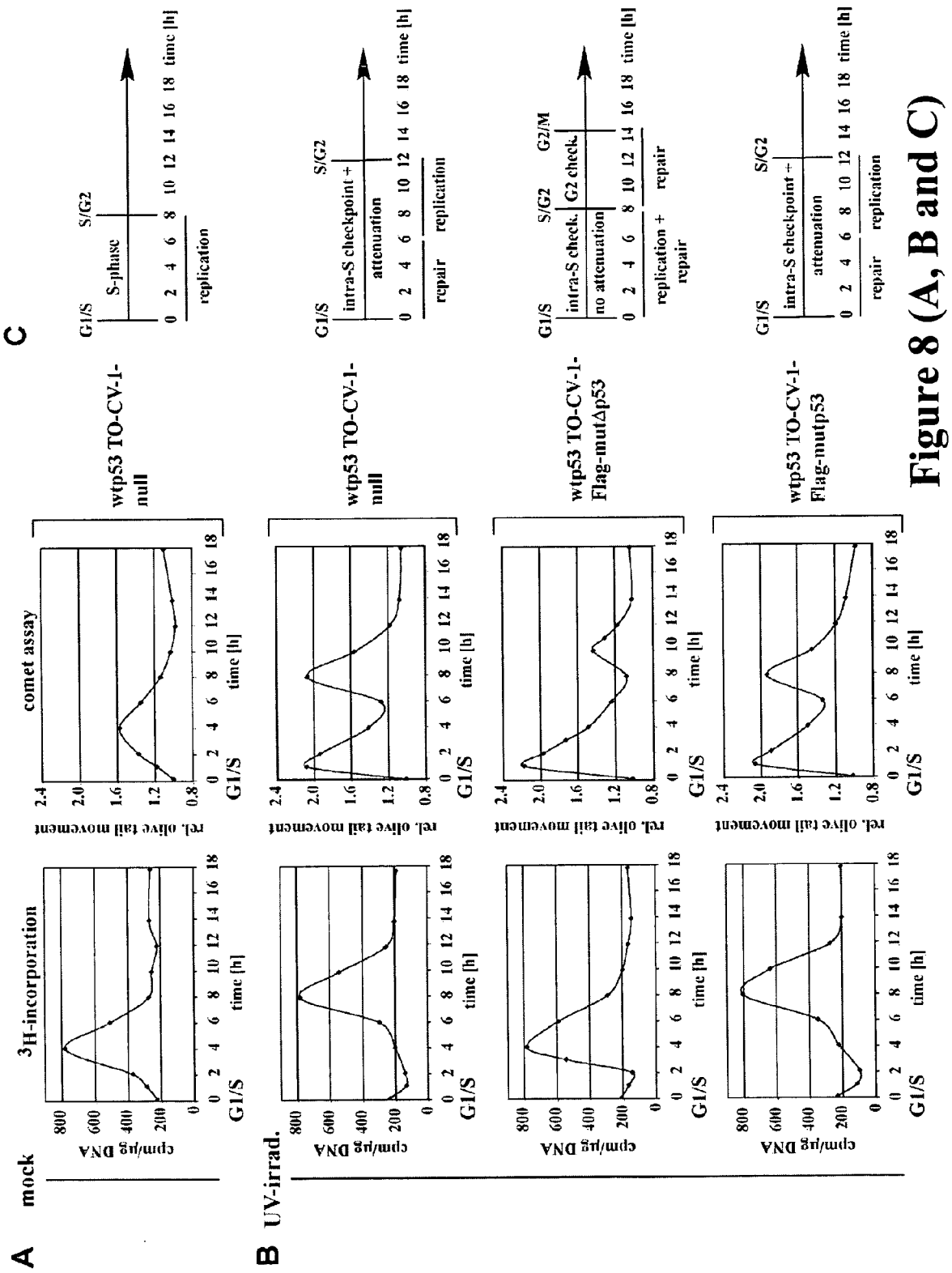
Figure 8 (A, B and C)

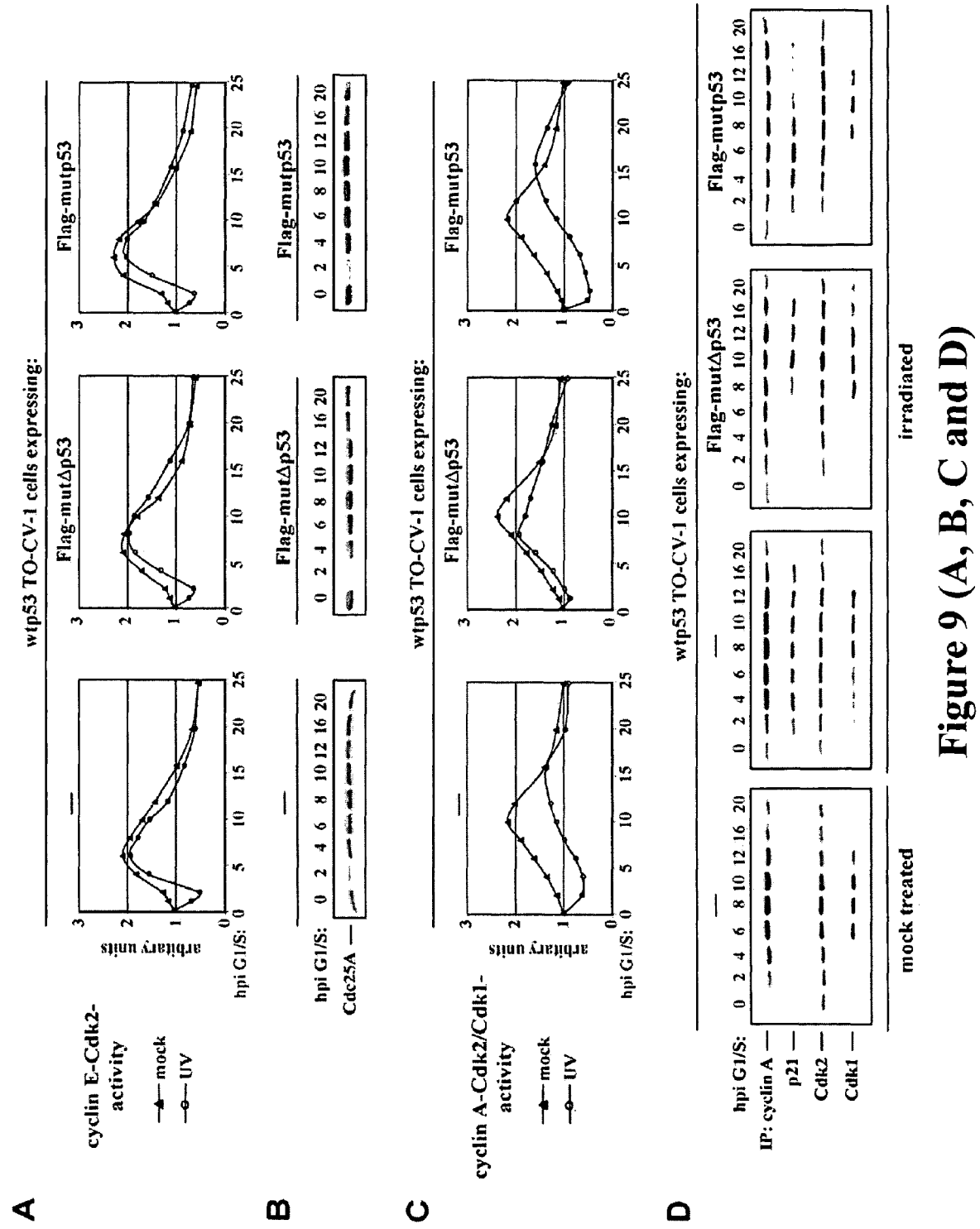
Figure 9 (A, B, C and D)

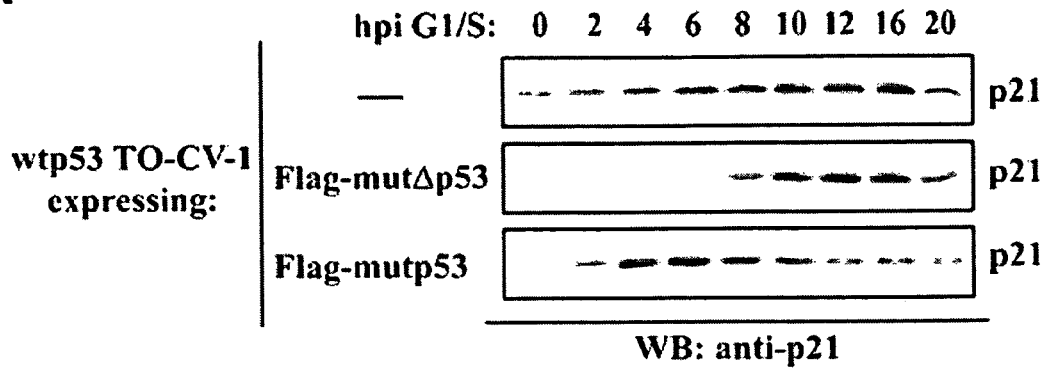
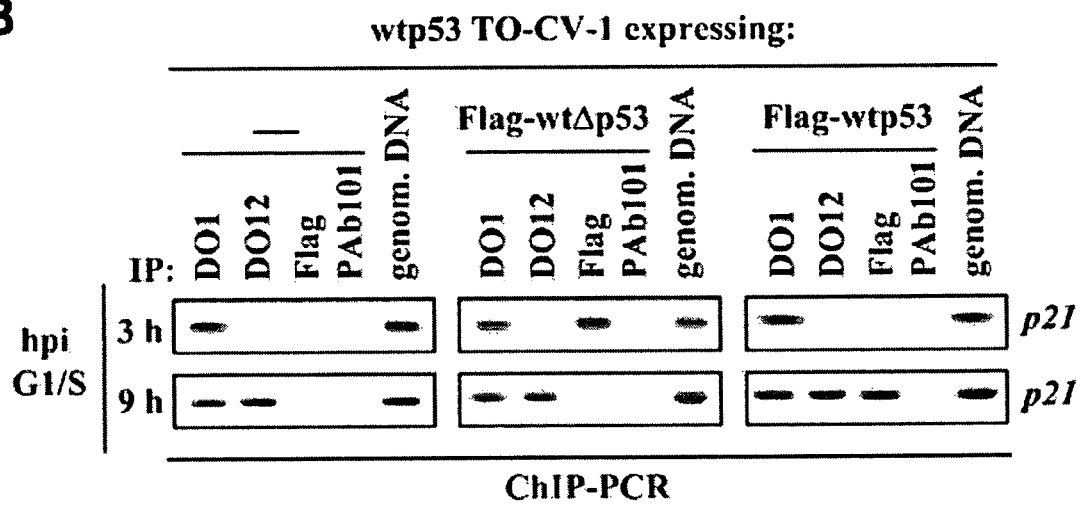
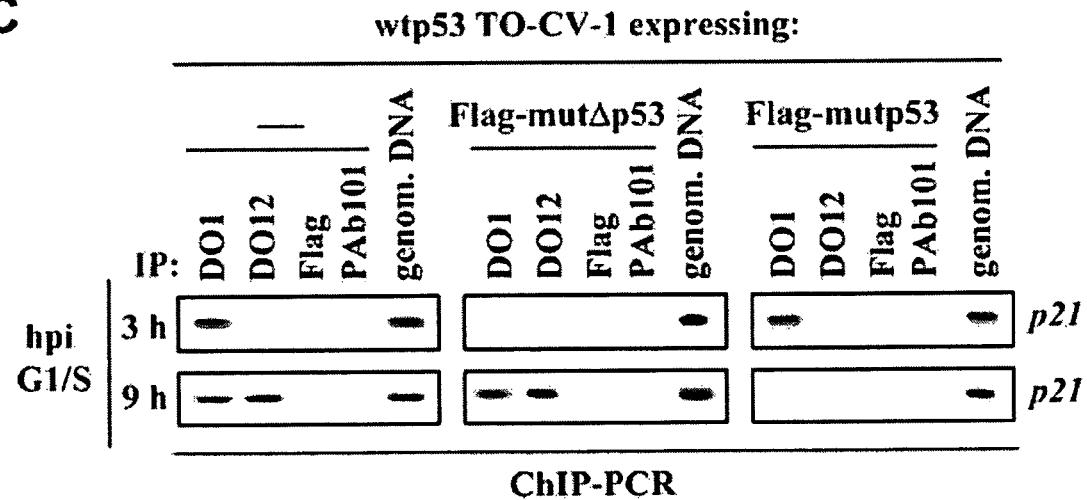
Figure 10 (A, B and C)

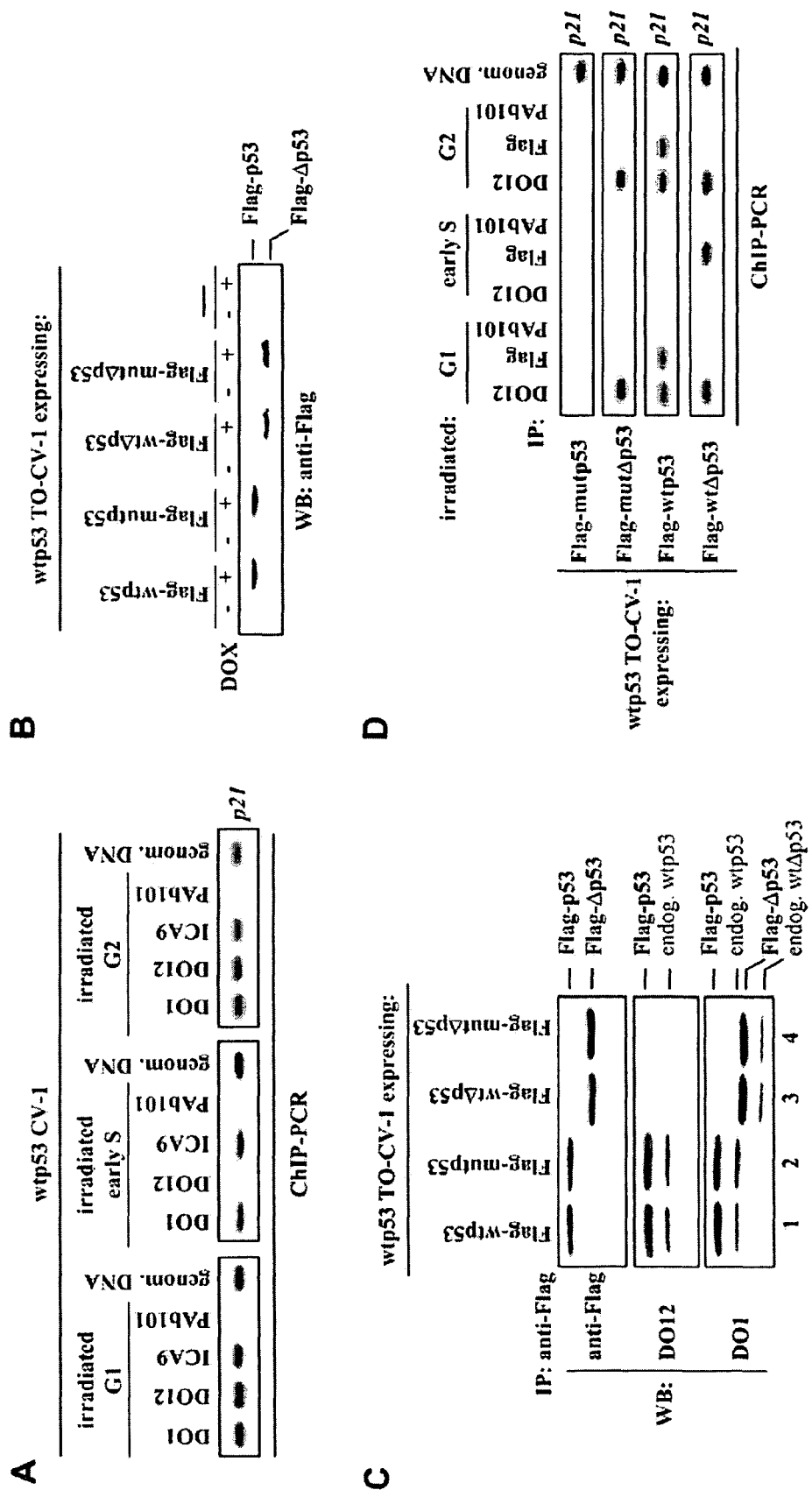
Figure 11 (A, B, C and D)

SEQUENCE LISTING

```
<160> NUMBER OF SEQ ID NOS: 26

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct

<400> SEQUENCE: 1
atcacactgg atgga                                                    15

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
agagtaacag gctaaggctt acct                                          24

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
tgtggctctg attggctttc tggccat                                       27

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct
```

```
<400> SEQUENCE: 4
gagctgtgat cataccactg ta                                          22

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ggacatgtct gtgctaatgc t                                           21

<210> SEQ ID NO 6
<211> LENGTH: 23
<212> TYPE: DNA
<213> ORGANISM: Artificial Sequence
<220> FEATURE:
<223> OTHER INFORMATION: Synthetic construct

<400> SEQUENCE: 6
agcttttcct cttgagctgg tca                                         23

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
ttcaatcgcc actgaacaca gct                                         23

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
tcacaagtta gacaagcctg gg                                          22

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
acgtgactgt ccaatgagca tct                                         23

<210> SEQ ID NO 10
<211> LENGTH: 31
<212> TYPE: DNA
<213> ORGANISM: Artificial Sequence
<220> FEATURE:
<223> OTHER INFORMATION: Synthtic Construct

<400> SEQUENCE: 10
caggactgtc aggaggaggc gagtgataag g                                31

<210> SEQ ID NO 11
<211> LENGTH: 31
<212> TYPE: DNA
```

```
<213> ORGANISM: Artificial Sequence
<220> FEATURE:
<223> OTHER INFORMATION: Synthetic Construct

<400> SEQUENCE: 11
gtgcgattct agctctcact tcaaggagag g                                    31

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
ccatggagga gccgcagtca g                                               21

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
cgcccatgca ggaactgtta                                                 20

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
cagtcagatc ctagcgtcga g                                               21

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ggtggtacag tcagagccaa                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
ctcctggccc ctgtcatcgt                                                 20

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
gctcagtggg ggaacaagaa c                                               21
```

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
tgaggttggc tctgactgta                                          20

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
agaatgtcag tctgagtcag g                                        21

<210> SEQ ID NO 20
<211> LENGTH: 39
<212> TYPE: DNA
<213> ORGANISM: Artificial Sequence
<220> FEATURE:
<223> OTHER INFORMATION: Synthetic Construct

<400> SEQUENCE: 20
tatatgaatt cgggatccca tggaggagcc gcagtcaga                     39

<210> SEQ ID NO 21
<211> LENGTH: 39
<212> TYPE: DNA
<213> ORGANISM: Artificial Sequence
<220> FEATURE:
<223> OTHER INFORMATION: Synthetic Construct

<400> SEQUENCE: 21
tatatgaatt cggtcagtct gagtcaggcc cttctgtct                     39

<210> SEQ ID NO 22
<211> LENGTH: 37
<212> TYPE: DNA
<213> ORGANISM: Artificial Sequence
<220> FEATURE:
<223> OTHER INFORMATION: Synthetic Construct

<400> SEQUENCE: 22
tcctcaccat catcacactg gatggagata tttcacc                       37

<210> SEQ ID NO 23
<211> LENGTH: 15
<212> TYPE: DNA
<213> ORGANISM: Artificial Sequence
<220> FEATURE:
<223> OTHER INFORMATION: Synthetic Construct

<400> SEQUENCE: 23
atcacactgg atgga                                               15

<210> SEQ ID NO 24
<211> LENGTH: 327
<212> TYPE: PRT
<213> ORGANISM: Homo sapiens

<400> SEQUENCE: 24

-continued

```
Met Glu Glu Pro Gln Ser Asp Pro Ser Val Glu Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys His Ser
225                 230                 235                 240

Ser Cys Met Gly Gly Met Asn Arg Arg Pro Ile Leu Thr Ile Ile Thr
                245                 250                 255

Leu Asp Gly Glu Tyr Phe Thr Leu Gln Ile Arg Gly Arg Glu Arg Phe
            260                 265                 270

Glu Met Phe Arg Glu Leu Asn Glu Ala Leu Glu Leu Lys Asp Ala Gln
            275                 280                 285

Ala Gly Lys Glu Pro Gly Gly Ser Arg Ala His Ser Ser His Leu Lys
        290                 295                 300

Ser Lys Lys Gly Gln Ser Thr Ser Arg His Lys Lys Leu Met Phe Lys
305                 310                 315                 320

Thr Glu Gly Pro Asp Ser Asp
                325
```

<210> SEQ ID NO 25
<211> LENGTH: 7
<212> TYPE: DNA
<213> ORGANISM: Artificial Sequence
<220> FEATURE:
<223> OTHER INFORMATION: Synthetic construct

<400> SEQUENCE: 25 cactgga                                                             7

<210> SEQ ID NO 26
<211> LENGTH: 984
<212> TYPE: DNA
<213> ORGANISM: Homo sapiens

```
<400> SEQUENCE: 26
atggaggagc cgcagtcaga tcctagcgtc gagcccctc tgagtcagga aacattttca         60
gacctatgga aactacttcc tgaaaacaac gttctgtccc ccttgccgtc ccaagcaatg        120
gatgatttga tgctgtcccc ggacgatatt gaacaatggt tcactgaaga cccaggtcca       180
gatgaagctc ccagaatgcc agaggctgct cccccgtgg ccctgcacc agcagctcct         240 acaccggcgg ccctgcacc agcccctcc tggccctgt catcttctgt ccttcccag           300 aaaacctacc agggcagcta cggtttccgt ctgggcttct tgcattctgg gacagccaag       360
tctgtgactt gcacgtactc ccctgccctc aacaagatgt tttgccaact ggccaagacc       420
tgccctgtgc agctgtgggt tgattccaca ccccgcccg gcacccgcgt ccgcgccatg        480
gccatctaca agcagtcaca gcacatgacg gaggttgtga ggcgctgccc ccaccatgag       540
cgctgctcag atagcgatgg tctggcccct cctcagcatc ttatccgagt ggaaggaaat      600
ttgcgtgtgg agtatttgga tgacagaaac acttttcgac atagtgtggt ggtgccctat      660
gagccgcctg aggttggctc tgactgtacc accatccact acaactacat gtgtaacagt      720
tcctgcatgg gcggcatgaa ccggaggccc atcctcacca tcatcacact ggatggagaa       780
tatttcaccc ttcagatccg tgggcgtgag cgcttcgaga tgttccgaga gctgaatgag       840
gccttggaac tcaaggatgc ccaggctggg aaggagccag gggggagcag ggctcactcc      900
agccacctga agtccaaaaa gggtcagtct acctcccgcc ataaaaaact catgttcaag      960
acagaagggc ctgactcaga ctga                                              984
```

HUMAN P53 SPLICE VARIANT DISPLAYING DIFFERENTIAL TRANSCRIPTIONAL ACTIVITY

CROSS-REFERENCE TO RELATED APPLICATIONS

This application is a Continuation in Part application of and claims priority to PCT International Application No: PCT/EP2004/003299 filed on Mar. 29, 2004, which in turn claims priority to European Patent Application No. 03007000.7 filed on Mar. 27, 2003, the contents of which are incorporatated by reference herein for all purposes.

BACKGROUND OF THE INVENTION

1. Field of Technology

The present invention relates to a p53 variant characterized in that it is capable of transactivating the p21- and 14-3-3σ-promoter but not the mdm2-, bax- and PIG3-promoter. In a preferred embodiment, said p53 variant is characterized in that exon 7, exon 8 and/or exon 9 are partially or entirely deleted. The present invention also relates to means for inhibiting the activity of this p53 variant which is useful for the therapy of cancer. Further increasing the amount of said p53 variant can increase DNA repair by extending the S phase cycle.

2. Discussion of Related Art

Activation of the tumor suppressor p53 after genotoxic insults leads to the induction of downstream events that provide a complex network of signals leading to cell cycle arrest or apoptosis. Both events are in large part due to p53-dependent transcriptional activation of several downstream genes including cell cycle regulators (e.g., p21, 14-3-3σ, Gadd45) and proapoptotic factors (e.g., bax and PIGs). Since both pathways are activated by p53-mediated transactivation of genes, regulatory mechanisms must exist to determine the choice of the appropriate target genes within a given cellular and physiological context. The complex regulatory web that mobilizes p53 after stress is continuously expanding and includes key checkpoint regulators such as the phosphatidylinositol 3-kinase family members ataxia telangiectasia mutated (ATM) and ATM-Rad3-related protein (ATR) as well as the downstream checkpoint kinases Chk2 and Chk1. Phosphorylation on serine (S) 20 of p53 by Chk2/Chk1 helps to stabilize p53 by uncoupling it from the Mdm2 ubiquitin ligase, while ATM/ATR-catalyzed phosphorylation on S-15 participates in the activation of p53.

The p53 tumor suppressor gene is mutated in a large fraction of human cancers, indicating that wild-type p53 (wtp53) function is required to limit tumor growth. Depending on the physiological circumstances, p53 can prevent growth through two mechanisms. First, p53 causes arrest in both the G1 and G2 phases of the cell cycle and second, p53 is involved in the induction of apoptosis. Both events are in large part due to p53-dependent transcriptional activation of several downstream genes including cell cycle regulators (e.g. p21, 14-3-3σ, Gadd45) and pro-apoptotic factors (e.g. bax and PIGs). It is not clear, how the transcriptional activity of p53 is regulated to induce growth arrest or apoptosis. However, distinct post-translational modifications of p53 such as phosphorylation, acetylation, O-glycosylation, proteolysis and/or binding of p53 to other proteins are most likely required to determine the promoter selectivity of p53. Since so far the mechanisms of selective activation of promoters of genes responsible for cell cycle regulation and apoptosis by p53 are not known, an adequate medical treatment of tumors associated with an aberrant expression or activity of p53 is difficult.

Thus, the technical problem underlying the present invention is to provide means for the treatment of cancer types associated with an aberrant expression/activity of p53.

SUMMARY OF THE INVENTION

The present invention relates to the isolation and characterization of a gene encoding a novel human isoform of the tumor suppressor p53 (Δp53) that is generated by alternative exon splicing.

In one aspect, the present invention relates to an isolated Δp53 protein encoded by a nucleotide sequence that lacks 198 nucleotides located in exons 7, 8 and 9.

In another aspect the present invention relates to an isolated nucleotide sequence encoding a p53 variant, wherein the nucleotide sequence comprises a nucleic acid sequence selected from the group consisting of:
  (a) SEQ ID NO: 26;
  (b) a nucleic acid sequence that has more than 95% identity to a nucleic acid sequence of SEQ ID NO 26;
  (c) a nucleic acid sequence fully complementary to a nucleic acid of (a); and
  wherein the isolated p53 variant transactivates the endogenous p21- and 14-3-3σ- but not the mdm2-, bax- and PIG3-promoter.

In yet another aspect, the present invention relates to an isolated Δp53 protein that transactivates the endogenous p21- and 14-3-3σ- but not the mdm2-, bax- and PIG3-promoter.

In a still further aspect, the present invention relates to an isolated Δp53 protein comprising an amino acid sequence according to SEQ ID NO: 24 or an amino acid sequence having at least 90% homology to SEQ ID NO: 24 and having the same functional activity transactivating the endogenous p21- and 14-3-3σ- but not the mdm2-, bax- and PIG3-promoter.

In another aspect, the invention further provides for a purified and isolated nucleic acid molecule encoding a mutated protein with homology to SEQ ID NO: 24.

A further aspect of the present invention relates to an S cell cycle phase arresting agent having an amino acid sequence of SEQ ID NO: 24 or at least 90% homology that transactivates the endogenous p21- and 14-3-3σ- but not the mdm2-, bax- and PIG3-promoter.

In yet another aspect, the present invention relates to a method for screening a potential cellular apoptosis inducing test compound for determining it utility as a therapeutic agent for increasing cell death, the method comprising:
  (a) contacting a cell which expresses a protein having an amino acid sequence SEQ ID NO: 24 or 95% homology having a function of transactivating the endogenous p21- and 14-3-3σ- but not the mdm2-, bax- and PIG3-promoter with the test compound; and;
  (b) determining the level of apoptosis activity of the cell, wherein an increase in apoptosis activity identifies a test compound that induces apoptotic activity.

In another aspect, the present invention further provides an expression vector comprising a polynucleotide sequence encoding amino acid sequence SEQ ID NO: 24 or a functionally active protein having at least 95% homology. In yet another aspect this expression vector is contained within a host cell for transforming the host cell for expressing the polypeptide.

In a further aspect, the present invention further relates to a purified antibody which binds to a polypeptide comprising an amino acid sequence of SEQ ID NO: 24 or 90% homology thereof and having the functional acitivty of SEQ ID NO. 24.

In yet another aspect, the present invention relates to a method of increasing apoptosis in human cells comprising:
    administering an antisera specific for p53 variant of SEQ ID NO: 24 in a sufficient amount to effect protein-protein interaction of p53 variant with p21.

In a still further aspect, the present invention relates to a method of decreasing apoptosis in human cells comprising:
    administering a p53 variant of SEQ ID NO: 24 in a sufficient amount to effect protein-protein interaction of p53 variant with p21.

Other features and advantages of the invention will be apparent from the following detailed description, drawings and claims.

BRIEF DESCRIPTION OF THE DRAWINGS

FIG. 1 RT-PCR reveals a novel alternatively spliced form of p53

Figure 2:
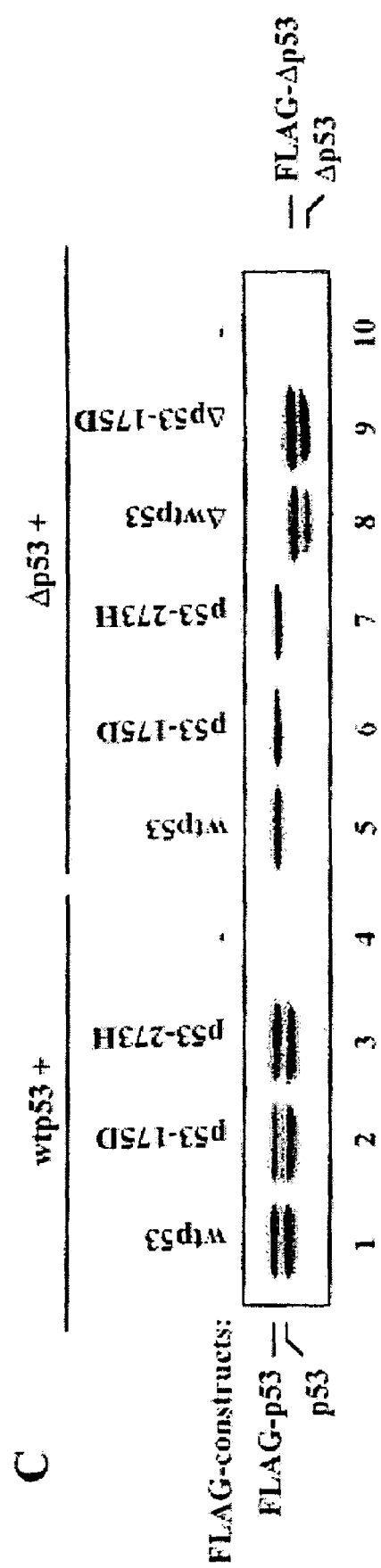

(A) RT-PCR analysis of RNAs derived from wtp53 expressing human peripheral blood (lane 2), primary rhesus kidney (lane 3), human (lane 4) and monkey (lane 5) cells and mutp53 expressing human (lanes 6 and 7) and rhesus (lane 8) cell lines. The amplified PCR fragment corresponding to full-length p53 (p53) and the isoform (Δp53) is indicated. (M) 100 bp DNA ladder (lane 1).

(B) Presentation of the sequenced exon-exon boundary of the 325 bp generated amplicon.

(C) Identification of the deletion junction CACTGGA (SEQ ID NO: 25), which derived from Exon 7 and 9.

(D) Schematic representation of alternatively spliced Δp53.

FIG. 2: Characterization of Δp53 at the protein level (A) Lysates derived from the wtp53 primary cell line PRK, wtp53 HSC93 cells, mutp53 cell lines A431, SW480 and LLC-MK2 cells were used to analyze the expression levels of full-length $p5^3$ and Δp53 before (−) and after γ-irradiation (+) by immunoblotting. The $p5^3$ proteins were detected with monoclonal anti-p53 antibodies DO1 (N-terminus), and ICA9 (C-terminus).

(B) Full-length p53 was immunoprecipitated with monoclonal antibody D012 (epitope is deleted in Δp53) to evaluate complex formation with Δp53. Immunoprecipitates were analyzed with rabbit polyclonal anti-p53 antibody "SAPU".

(C) H1299 cells were co-transfected with pCDNA3 and pCMV-TagB2 constructs. The FLAG-tagged p53 proteins were immunoprecipitated with monoclonal anti-FLAG antibody M2 as indicated. Complex formation of the FLAG-tagged p53 proteins with untagged full-length wtp53 (lanes 1-4) or untagged Δp53 (lanes 5-10) was analyzed with polyclonal anti-p53 antibody "SAPU". The control experiments did not contain FLAG-tagged full-length p53 (lane 4) or FLAG-tagged Δp53 (lane 10).

FIG. 3: Selective transactivation of endogenous p53-inducible promoters by Δp53

(A) Lysates derived from H1299 cells transfected with pCDNA3 constructs as indicated were analyzed for p53 expression by Western blot with polyclonal anti-p53 antibody "SAPU". Lysate prepared from γ-irradiated HSC93 cells served as positive control (lane 1).

(B) Transactivation of endogenous p53-inducible promoters p21, 14-3-3σ, mdm2, bax and PIG3 was analyzed by immunoblotting in H1299 cells transfected with pCDNA3 constructs as indicated.

FIG. 4: Selective promoter binding of wtΔp53 in irradiated mutp53 cells (A) AWtp53 CV-1, (C) WtΔp53 expressing mutp53 A431 and (E) MutΔp53 expressing mutp53 LLC-MK2 cells were γ-irradiated, treated with formaldehyde and processed as described in methods for ChIP. Full-length p53 and Δp53 were precipitated with anti-p53 monoclonal antibodies DO1 and ICA9 (lanes 1 and 3), whereas antibody DO12 was utilized to precipitate only full-length p53 (lanes 2). Non-p53 specific monoclonal antibody PAb101 served as negative control (lanes 4). Immunoprecipitates were analyzed by Western blotting with polyclonal anti-p53 antibody "SAPU". (B), (D), (F) The p53 associated p21-, 14-3-3σ, mdm2-, bax- and PIG3-promoters were identified by PCR. Genomic DNA served as marker for the ChIP-PCR products. The ethidium bromide stained bands represent relative amount of the promoter DNA recovered by PCR amplification of DNA extracted from the immunoprecipitates (A, C, E).

FIG. 5 Induction of $p^{21}$ and 14-3-3σ in irradiated mutp53 cells

Wtp53 CV-1, wtΔp53 expressing mutp53 A431 and mutΔp53 expressing mutp53 LLC-MK2 cells were γ-irradiated.

(A) The protein levels of p21, 14-3-3σ, and mdm2 were determined at the indicated time points after γ-irradiation (hpi) by immunoblotting. Equal protein loading was confirmed by 14-3-3σ expression.

(B) Western blot analysis of the protein levels bax and PIG3 after γ-irradiation at the indicated time points (hpi).

FIG. 6 Irradiation of wtΔp$^{53}$ expressing mutp53 cells induces polyploidization (A) Human lymphoma cell lines HSC93 (wtp53■), HL60 (p53 negative ○), CEM (mutp53+mutΔp53▲) and Karpas-299 (mutp53+wtΔp53✻) were γ-irradiated and scored for death after staining with trypan blue at the indicated time points.

(B) Same cell lines and A431 (mutp53+wtΔp53) cells were γ-irradiated, harvested at the indicated time points, stained with propidium iodide and analyzed by FACS. Peaks corresponding to 2N, 4N and 8N are labeled accordingly.

FIG. 7. Sequence listing (A) the amino acid sequence of the novel Δp53 of the present invention (SEQ ID NO: 24); (B) comparison with wild type p53 and (C) nucleotide sequence encoding Δp53 (SEQ ID NO: 26).

FIG. 8: Uncoupling of Repair and Replication Activities Depends on Functional Δp53

(A) $^3$H incorporation (left panel) was measured in Dox-induced, G1/S-mock treated wtp53 TO-CV-1 null cells. Cells were labeled with $^3$H for 60 min at the indicated times thereafter (x axis) and the resulting ratios of $^3$H cpm to μg DNA were a measure of DNA synthesis (y axis). Alkaline comet assay (right panel) was performed at the indicated time points (x axis); the relative olive tail moment, which reflects ssDNA breakage, is depicted on the y axis.

(B) $^3$H incorporation (left panels) was measured in Dox-induced, G1/S-UV-irradiated wtp53 TO-CV-1 null, -Flag-mutΔp53, and -mutp53 cells to determine replication activity as in (A). Alkaline comet assays (right panels) were carried out as in (A).

(C) Schematic representation of replication and repair events of Dox-induced, G1/S-mock- or -UV-irradiated wtp53 TO-CV-1 cell lines.

FIG. 9: ΔV53-Transactivated $p^{21}$ Downregulates Cyclin A-Cdk2 Activity (A and C) Dox-induced, G1/S-mock- or UV-irradiated wtp53 TO-CV-1-Flag-mutΔp53, -mutp53, null (−) cells were harvested at the indicated time points (x axis) and subjected to target bound cyclin E-Cdk2 (A) and cyclin A-Cdk2/1 (C)

assays. The relative amount of kinase activity normalized to the kinase activity measured from cells at 0 hr is shown (y axis).

(B) Cdc25A protein level determined from Dox-induced, G1/S-UV-irradiated wtp53 TO-CV-1 cells as in (A) by Western blot.

(D) Analysis of cyclin A association with kinases Cdk2, Cdk1, and p21 in Dox-induced, G1/S-UV-irradiated wtp53 TO-CV-1 cells as in (A) by IP-Western blot. Analysis of mock-treated wtp53 TO-CV-1 null cells is shown in the first panel.

FIG. 10: Δp53 and p53 Are Activated and Inactivited Consecutively (A) Analysis of $p^{21}$ expression in Dox-induced, G1/S-UV-irradiated wtp53 TO-CV-1-Flag-mutΔp53, -mutΔp53, null (−) cells by Western blot at the indicated hpi. (B) Dox induced, G1/S-UV-irradiated wtp$^{53}$ TO-CV-1-Flag-wtΔp53, -mutp53, null (−) cells were treated with formaldehyde 3 and 9 hpi and processed for ChIP. Crosslinked Δp53/p53-DNA complexes were precipitated with anti-p53 DO1, anti-fl p53 DO12, and anti-Flag M2 antibodies; anti-T-Ag antibody PAb101 served as negative control.

(C) Dominant-negative effect of Dox-induced Flag-mutΔp53 and -mutp53 expression was analyzed by ChIP-PCR as in (B).

FIG. 11: Differential Transcriptional Activity of Endogenous Δp53 Is S Phase Specific (A)

Wtp53 CV-1 cells, UV-irradiated in G1, early S, and G2, were treated with formaldehyde 2 hpi and processed for ChIP. Crosslinked Δp53/p53-DNA complexes were precipitated with anti-p53 antibodies and associated p21 promoter DNA was identified by PCR.

(B) Inducible wtp53 TO-CV-1-Flag-wtp53, -mutp53, -wtΔp53, -mutΔp53 or null (−) cells (−)/(+) Dox were analyzed for ectopic Flag-p53 protein expression by Western blot.

(C) Immunoprecipitated Flag-tagged p53 proteins derived from Dox induced wtp53 TO-CV-1 cells as in (B) were analyzed for oligomerization with endogenous wtp53 and wtΔp53. Immunoprecipitated Flag-p53 proteins were visualized with anti-Flag antibody M2. Associated endogenous wtp53 and wtΔp53 (shown in roman) was analyzed with anti-p53 antibody DO1. Antibody DO12 was used to detect only p53.

(D) Dox-induced wtp53 TO-CV-1 cells as in (B) were UV irradiated in G1, early S, and G2, treated with formaldehyde 2 hpi, and processed for ChIP. Flag-tagged p53 proteins were precipitated with antibody M2; antibody D012 was used to precipitate only p53. T-Ag-specific antibody PAb101 served as negative control. Associated p21 promoter DNA was identified by PCR.

DETAILED DESCRIPTION OF THE INVENTION

In a first embodiment, the present invention relates to a nucleic acid molecule encoding a p53 variant characterized in that it is capable of transactivating the p21- and 14-3-3σ-promoter but (in contrast to the native form of p53) not the mdm2-, bax- and PIG3-promoter. Preferably, the variant has amino acid sequence residues of SEQ ID NO: 24 or at least 95% homology thereof.

The nucleic acid molecules of the invention can be both DNA and RNA molecules. Suitable DNA molecules are, for example, genomic or cDNA molecules. It is understood that all nucleic acid molecules encoding all or a portion of the p53 variant are also included, as long as they encode a polypeptide with the biological activity of said p53 variant. The nucleic acid molecules of the invention can be isolated from natural sources or can be synthesized according to known methods. Based on the finding of the present invention that the transactivating activities of p53 can be separated, i.e. that the transactivating activity for the mdm2-, bax- and PIG3-promoter can be eliminated without effecting its transactivating activity for the p21- and 14-3-3σ-promoter, the person skilled in the art can generate a nucleic acid molecule encoding a p53 variant of the present invention by means of conventional molecular biological processes as, e.g., described in Sambrook et al., 1992, Molecular Cloning, A Laboratory Manual, $2^{nd}$ edition Cold Spring Harbor Laboratory Press, Cold Spring Harbor, N.Y.), i.e. the skilled person can introduce different mutations such as deletions into the nucleic acid molecule encoding the wild-type form of p53. The nucleic acid sequence of p53 wild-type is well known to persons skilled in the art.

The term "variant" as used herein comprises p53 variants (a) the amino acid sequence of which corresponds to the amino acid sequence of the wild-type p53 except that part of the protein carrying the mutation (e.g., deletion) leading to loss of the transactivating function for the mdm2-, bax- and PIG3-promoter or (b) the amino acid sequence of which shows a high level of identity to the amino acid sequence of the wild-type p53 except that part of the protein carrying the mutation (e.g., deletion) leading to loss of the transactivating function for the mdm2-, bax- and PIG3-promoter sequences. Identity hereby means an amino acid sequence identity of at least 80% and preferably more than 90%. The deviations to the wild-type nucleic acid molecules may have been produced by deletion, substitution, insertion or recombination. The nucleic acid molecules of (b) encode p53 variants having substantially the same biological activity as the p53 variant of (a).

For the manipulation in prokaryotic cells by means of genetic engineering the nucleic acid molecules of the invention or parts of these molecules can be introduced into plasmids allowing a mutagenesis or a modification of a sequence by recombination of DNA sequences. By means of conventional methods (cf. Sambrook et al., 1992, Molecular Cloning: A Laboratory Manual, $2^{nd}$ edition, Cold Spring Harbor Laboratory Press, NY, USA) bases can be exchanged and natural or synthetic sequences can be added. In order to link the DNA fragments with each other adapters or linkers can be added to the fragments. Furthermore, manipulations can be performed that provide suitable cleavage sites or that remove superfluous DNA or cleavage sites. If insertions, deletions or substitutions are possible, in vitro mutagenesis, primer repair, restriction or ligation can be performed. As analysis method usually sequence analysis, restriction analysis and other biochemical or molecular biological methods are used.

In a preferred embodiment, the present invention relates to a nucleic acid molecule encoding a p53 variant of the invention characterized in that exon 7, exon 8 and/or exon 9 are partially or entirely deleted. Preferably, this deletion does not effect the reading frame of the 3'located exons (e.g., residual part of exon 9 and exon 10 etc.).

In a more preferred embodiment, the present invention relates to a nucleic acid molecule encoding a p53 variant of the invention characterized in that the variant comprises the amino acid sequence as depicted in FIG. 7.

The present invention also relates to an antisense RNA sequence characterized in that it is complementary to an mRNA transcribed from a nucleic acid molecule of the present invention or a part thereof and can selectively bind to said mRNA, said sequence being capable of inhibiting the synthesis of the p53 variant encoded by said nucleic acid molecules, and a ribozyme characterized in that it is complementary to an mRNA transcribed from the nucleic acid molecule of the present invention or a part thereof and can selectively bind to and cleave said mRNA, thus inhibiting the synthesis of the p53 variant encoded by said nucleic acid molecules.

Ribozymes which are composed of a single RNA chain are RNA enzymes, i.e. catalytic RNAs, which can intermolecularly cleave a target RNA, for example the mRNA transcribed from a gene encoding a p53 variant. It is now possible to construct ribozymes that are able to cleave the target RNA at a specific site by following the strategies described in the literature. (see, e.g., Tanner et al., in: Antisense Research and Applications, CRC Press Inc. (1993), 415-426). The two main requirements for such ribozymes are the catalytic domain and regions which are complementary to the target RNA and which allow them to bind to its substrate, which is a prerequisite for cleavage. Said complementary sequences, i.e., the antisense RNA or ribozyme, are useful for repression of expression of the p53 variant of the invention. Preferably, the antisense RNA and ribozyme of the invention are complementary to the coding region of the p53 variant mRNA. Preferably these molecules are complementary to a region that can not be found in the wild-type p53 mRNA, e.g., an mRNA region comprising a nucleotide sequence generated by alternative splicing as shown in FIG. 1(C). The person skilled in the art provided with the sequences of the nucleic acid molecules of the present invention will be in a position to produce and utilize the above described antisense RNAs or ribozymes. The region of the antisense RNA and ribozyme, respectively, which shows complementarity to the mRNA transcribed from the nucleic acid molecules of the present invention preferably has a length of at least 10, in particular of at least 15 and particularly preferred of at least 50 nucleotides.

The invention furthermore relates to vectors containing the nucleic acid molecules of the invention. Preferably, they are plasmids, cosmids, viruses, bacteriophages and other vectors usually used in the field of genetic engineering. Vectors suitable for use in the present invention include, but are not limited to the T7-based expression vector for expression in bacteria, the pMSXND expression vector for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an RNA in prokaryotic and/or eukaryotic cells that can be translated. The nucleotide sequence to be transcribed can be operably linked to a promotor like a T7, metallothionein I or polyhedrin promotor.

In a further embodiment, the present invention relates to recombinant host cells transiently or stably containing the nucleic acid molecules or vectors of the invention. A host cell is understood to be an organism that is capable to take up in vitro recombinant DNA and, if the case may be, to synthesize the proteins encoded by the nucleic acid molecules of the invention. Preferably, these cells are prokaryotic or eukaryotic cells, for example mammalian cells, bacterial cells, insect cells or yeast cells. The host cells of the invention are preferably characterized by the fact that the introduced nucleic acid molecule of the invention either is heterologous with regard to the transformed cell, i.e. that it does not naturally occur in these cells, or is localized at a place in the genome different from that of the corresponding naturally occurring sequence. Furthermore, the host cells of the invention are understood to be transgenic mammals, preferably rodents such as mice or rats expressing proteins encoded by the nucleic acid molecules of the invention. Such mammals can be obtained by methods well-known to persons skilled in the art.

A further embodiment of the invention relates to a p53 variant which is encoded by a nucleic acid molecule of the invention, as well as to methods for its production, whereby, e.g., a host cell of the invention is cultivated under conditions allowing the synthesis of the protein and the protein is subsequently isolated from the cultivated cells and/or the culture medium. Isolation and purification of the recombinantly produced p53 variant may be carried out by conventional means including preparative chromatography and affinity and immunological separations involving affinity chromatography with monoclonal or polyclonal antibodies, e.g. with the anti-p53 monoclonal antibodies DO1, DO12 or ICA9 described in Example 1(C) or an antibody which is specific for a p53 variant according to the present invention.

As used herein, the term "p53 variant" includes not only recombinantly produced proteins but includes isolated naturally occurring proteins, synthetically produced proteins, or proteins produced by a combination of these methods. Means for preparing such proteins are well understood in the art. The p53 variants are preferably in a substantially purified form. A recombinantly produced p53 variant, including the secreted protein, can be substantially purified by the one-step method described in Smith and Johnson, Gene 67:31-40 (1988).

In still a further embodiment, the present invention relates to an inhibitor of a p53 variant of the present invention which is an antibody. Preferably, said antibody recognizes and binds to the p53 variant of the invention but not to the wild-type p53 protein. For example, the antibody might recognize an epitope of the p53 variant which does not occur in the wild-type p53, preferably an epitope comprising an amino acid sequence encoded by the nucleic acid sequence formed by alternative splicing as shown in FIG. 1(C). The term "antibody" as used herein, preferably, relates to antibodies which consist essentially of pooled monoclonal antibodies with different epitopic specificities, as well as distinct monoclonal antibody preparations. Monoclonal antibodies are made from an antigen containing fragments of a p53 variant protein of the invention, preferably a fragment comprising an amino acid sequence which is not present in wild-type p53, by methods well known to those skilled in the art (see, e.g., Kohler et al., Nature 256 (1975), 495). As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316-325 (1983).) Thus, these fragments are preferred, as well as the products of a FAB or other immunoglobulin expression library. Moreover, antibodies of the present invention include chimeric, single chain, and humanized antibodies.

The present invention also relates to a pharmaceutical composition containing a compound of the invention, i.e., antisense RNA such as SI RNA, ribozyme or antibody. For example, administration of an antibody directed to a p53 variant of the invention can bind and reduce overproduction of the protein. Preferably, in case of tumors characterized by the presence of a p53 variant of the present invention, e.g., wtΔp53, radio- and/or chemotherapy is combined with the application of a pharmaceutical composition of the present invention in order to avoid the undesired activation of, e.g., wtΔp53.

The pharmaceutical composition, preferably, additionally contains suitable pharmaceutical carriers. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. The route of administration, of course, depends on the nature of the disease and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of the disease, general health and other drugs being administered concurrently.

The delivery of the antisense RNAs such as SI RNAs, ribozymes or nucleic acids encoding an antibody of the invention can be achieved by direct application or, preferably, by using a recombinant expression vector such as a chimeric virus containing these compounds or a colloidal dispersion system. By delivering these nucleic acids to the desired target, the intracellular expression of a p53 variant and, thus, the level of the p53 variant can be decreased resulting in the inhibition of the negative effects of the p53 variant as regards proliferation of tumor cells, e.g., release of high amount of anti-apoptotic factors, initiation of an uncoordinated cell cycle, formation of polyploid giant cells etc.

The above nucleic acids can be administered directly to the target site, e.g., by ballistic delivery, as a colloidal dispersion system or by catheter to a site in artery. The colloidal dispersion systems which can be used for delivery of the above nucleic acids include macromolecule complexes, nanocapsules, microspheres, beads and lipid-based systems including oil-in-water emulsions, (mixed) micelles, liposomes and lipoplexes. The preferred colloidal system is a liposome. The composition of the liposome is usually a combination of phospholipids and steroids, especially cholesterol. The skilled person is in a position to select such liposomes which are suitable for the delivery of the desired nucleic acid molecule. Organ-specific or cell-specific liposomes can be used in order to achieve delivery only to the desired metastasizing tumor. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention, monoclonal antibodies are preferably used to target liposomes to specific tumors via specific cell-surface ligands.

The antisense RNAs such as SI RNAs, ribozymes or nucleic acids encoding an antibody of the present invention can also be applied by gene therapy. Preferred recombinant vectors useful for gene therapy are viral vectors, e.g. adenovirus, herpes virus, vaccinia, or, more preferably, an RNA virus such as a retrovirus, or synthetic vectors such as pEPI-1(Piechazek, C. et al., Nucl. Acids Res. 27(1999), 426-428). Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotid encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the target organ to be treated, the nucleic acids encoding, e.g. an antisense RNA such as SI RNA, ribozyme or antibody can also be operably linked to a tissue specific promoter and used for gene therapy. Such promoters are well-known to persons skilled in the art.

A preferred medical use of the above discussed compounds is the treatment of tumor characterized by the presence of a p53 variant of the present invention, e.g., wtΔp53, preferably a class II mutp53 tumor. As used herein, the term "class II mutp53 tumor" means an mutp53 tumor wherein alternative splicing removes an inactivating p53 mutation resulting in the synthesis of a p53 variant with the biological activities listed before.

The present invention also relates to a diagnostic composition containing an oligonucleotide probe which is capable of specifically hybridizing to a part of the nucleic acid molecule of the present invention or an antibody of the invention which is capable of specifically binding to a p53 variant of the invention. The terms "specifically hybridizing" and "specifically binding" mean that the oligonucleotide probe does not hybridize with a nucleic acid sequence encoding wild-type p53 and that the antibody does not bind to wild-type p53 protein, respectively. Said oligonucleotide probes have a length of at least 10, in particular of at least 15 and particularly preferred of at least 50 nucleotides. Said oligonucleotide probes can also be used, for example, as primers for a PCR reaction. The person skilled in the art is in a position to design suitable oligonucleotide probes and immunogens for generating an antibody based on the information as regards the nucleotide sequence and amino acid sequence, respectively, of wild-type p53 and p53 variants of the present invention.

In a preferred embodiment, the oligonucleotide probe of the diagnostic composition of the invention comprises the nucleic acid sequence ATC ACA CTG GAT GGA (SEQ ID NO 1) or the complementary sequence thereof.

The target cellular component, i.e. a p53 variant according to the present invention or a p53 variant encoding mRNA, e.g., in biological fluids or tissues, may be detected directly in situ or it may be isolated from other cell components by common methods known to those skilled in the art before contacting with a probe. Detection methods include Northern blot analysis, RNase protection, in situ methods, PCR, LCR, immunoassays and other detection assays that are known to those skilled in the art.

The probes can be detectably labeled, for example, with a radioisotope, a bioluminescent compound, a chemiluminescent compound, a fluorescent compound, a metal chelate, or an enzyme.

p53 variant expression in tissues can be studied with classical immunohistological methods (Jalkanen et al., J. Cell. Biol. 101 (1985), 976-985; Jalkanen et al., J. Cell. Biol. Ad) (1987), 3087-3096). Other antibody based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin. In addition to assaying p53 variant levels in a biological sample, a p53 variant can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. A protein-specific antibody or antibody fragment, which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells that contain the specific protein. In vivo tumor imaging is described in S. W. Burchiel et al., "Immunopharmacokinetics of Radiolabeled Antibodies and Their Fragments." (Chapter 13 in 30 Tumor Imaging: The Radiochemical Detection of Cancer, S. W. Burchiel and B. A. Rhodes, eds., Masson Publishing Inc. (1982)).

Preferably, the oligonucleotide probe or antibody of the present invention are used for the preparation of a diagnostic composition for diagnosing a tumor characterized by the presence of a p53 variant according to the invention, e.g., wtΔp53, preferably a class II mutp53 tumor, or a predisposition to such a tumor.

It can be expected that due to the expression of wtΔp53 in particular cancer cells, treatment of such cancers by radio- or chemotherapy might result in an uncoordinated cell cycle that is followed by polyploidization and clonogenic survival, thus might have an effect. Accordingly, a further use of the oligonucleotides/antibodies of the present invention is the evaluation whether the treatment of a tumor by radio- or chemotherapy might have undesired effects.

For use in the diagnostic research discussed above, kits are also provided by the present invention. Such kits are useful for the detection of a target cellular component, which is a p53 variant or a p53 variant encoding mRNA. Said kits comprise a probe for detection of a p53 variant or a p53 variant encoding mRNA. The probe can be detectably labeled. Such probe may be an antibody or oligonucleotide specific for a p53 variant or a p53 variant encoding mRNA. In a preferred embodiment, said kit contains a p53 variant specific antibody and allows said diagnosis by ELISA and contains the antibody bound to a solid support, for example, a polystyrene microtiter dish or nitrocellulose paper, using techniques known in the art. Alternatively, said kits are based on a RIA and contain said antibody marked with a radioactive isotope. In a preferred embodiment of the kit of the invention, the anti-p53 variant-antibody is labeled with enzymes, fluorescent compounds, luminescent compounds, ferromagnetic probes or radioactive compounds. The kit of the invention may comprise one or more containers filled with, for example, one or more probes of the invention.

The physiological implication of Δp53 was elucidated in human mutp53 tumor cells, where p53 contains one of the most frequent "hotspot" mutations in exon 8. In such cells, alternative splicing generates "wild-type"-Δp53 that lacks the inactivating mutation of full-length p53. Following irradiation, "wild-type"-Δp53 counteracts apoptosis due to upregulation of p21 and 14-3-3σ, leads to polyploidization and promotes survival of DNA-damaged tumor cells. A plasmid encoding Δp53 (plasmid PCRII-TOPOSp6-deltap53; DSM 15482) has been deposited under Budapest Treaty on Mar. 6, 2003.

The 984-bp transcript transcribed from Δp53 was found in human, African green monkey and Rhesus monkey (FIG. 1A) but not in mouse, hamster, woodchuck and guinea pig, most likely because the donor site-like splicing-cassette and the acceptor site-like splicing cassette CACTGGA (SEQ ID NO: 25) are not present in rodent. In addition, "blast"-analysis of p53 showed that the two splice-cassettes CACTGGA can be found in sheep, pig, bovine and whale but not in chicken, rabbit, cat and dog indicating that expression of Δp53 might be restricted to some species. Furthermore, in all species, which have the two splice-cassettes in p53, the distance between the start of the donor site-like splicing-cassette and the acceptor site-like splicing cassette is exactly 198 bp (FIG. 1C). The finding suggests that in addition to the two splicing-cassettes, the length of the spacer between the two splicing-cassettes containing the sequence CACTGGA is required for the alternative splicing event in p53.

Figure 6A:
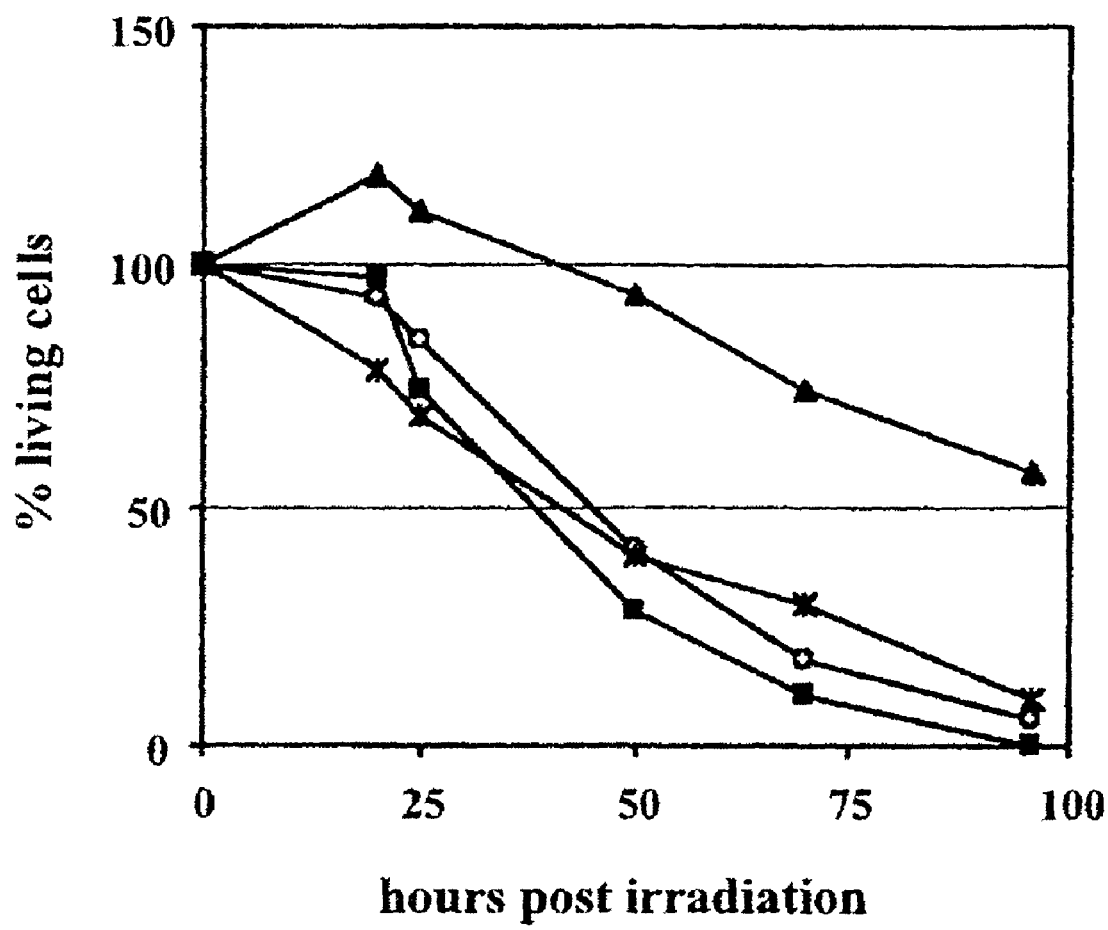
Figure 6B:
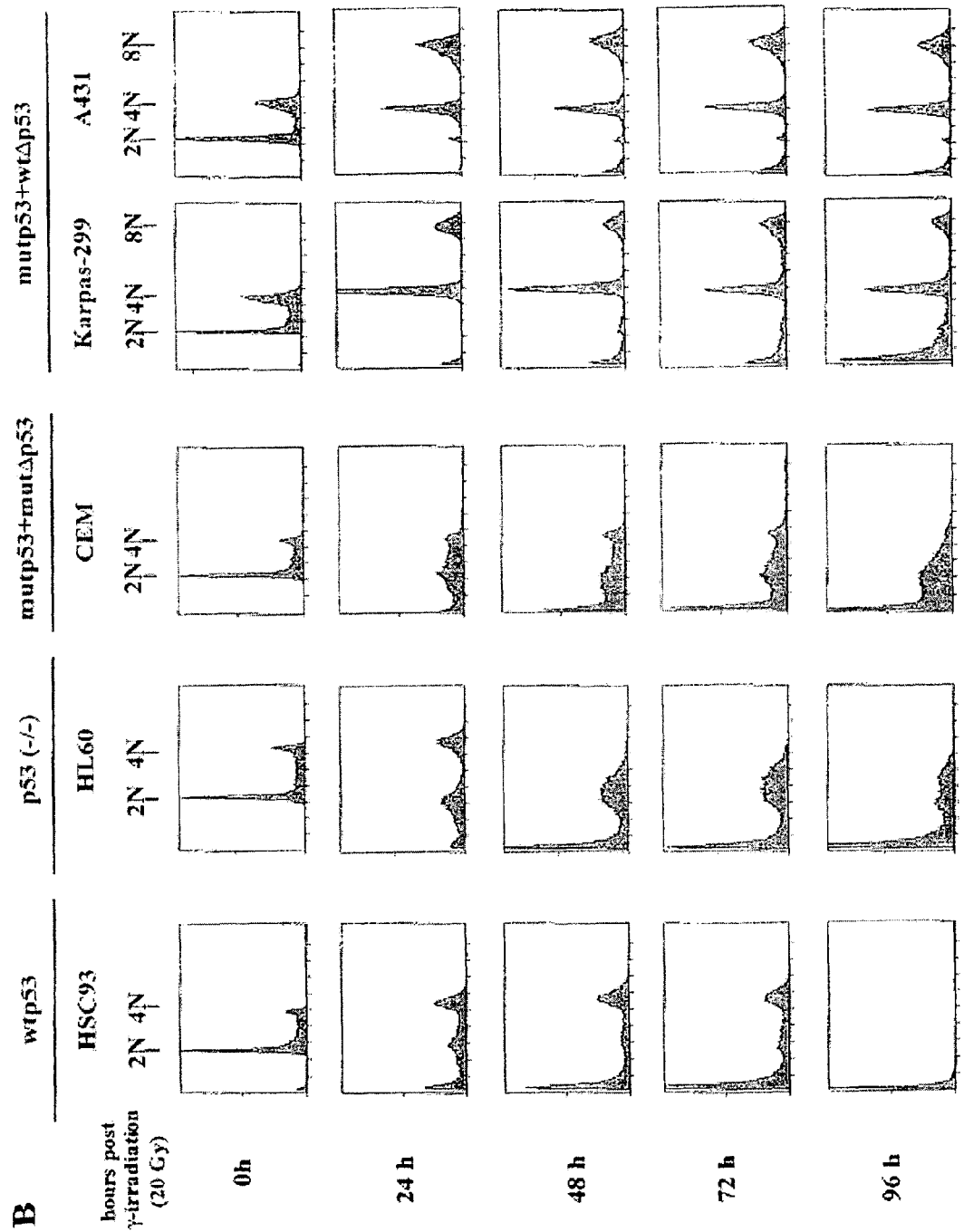

Transient transfection experiments having the results presented herein demonstrated that Δp53, which is readily detectable at the protein level and forms homo-oligomers but not hetero-oligomers (FIG. 2) transactivates the p21- and 14-3-3σ-promoter but not the mdm2-, bax- and PIG3-promter (FIG. 3B). Thus, unlike full-length p53 the p53-isoform displays differential transcriptional activity per se. The physiological implication of the differential transcriptional activity of the novel p53-isoform was examined in y-irradiated mutp53 cells. Two different classes of mutp53 tumor cell lines were used for the investigation: class I mutp53 tumor cell lines express mutΔp53 since the p53 mutation is located outside of the splice area and class II mutp53 tumor cell lines express wtΔp53 because the p53 mutation is removed by alternative splicing. ChIP-PCR and immunoblotting demonstrated that wtΔp53 but not mutΔp53 bound and transactivated selectively the endogenous p21- and 14-3-3σ-promoter (FIGS. 4 and 5). As shown recently, in DNA damaged cells, the Cdk inhibitory activity of p21 is required to prevent apoptosis and 14-3-3σ, is involved in the regulation of the progression of apoptosis by affecting the distribution of the pro-apoptotic protein. The results presented here show that human class I mutp53 and p53$^{-/-}$ cells, which are deficient in the transcriptional activation of anti-apoptotic factors p21 and 14-3-3σ, are sensitive to DNA damage and die quickly. In contrast, in irradiated wtΔp53 expressing mutp53 cells, transcriptional activation of p21 and 14-3-3σ counteracts apoptosis and promotes additional rounds of DNA synthesis resulting in a significant cell population with a DNA content of 8N (FIG. 6B). However, in severely DNA damaged wtp53 cells the p53-dependent apoptotic signal overrides the p53-mediated survival mechanism (FIG. 6A). These results confirm the finding that in the absence of pro-apoptotic factors, p53-dependent induction of p21 and 14-3-3σ counteracts apoptosis, allows further replicative rounds of DNA synthesis and thereby overrides genomic stability.

These results have important implications for cancer therapy. The p53 mutations that occur commonly in cancer abrogate part of the normal responses to DNA damage, i.e. induction of p21, 14-3-3σ, bax and PIG3. However, in class II mutp53 tumor cells where alternative splicing generates functional wtΔp53, genotoxic stress activates the differential transcriptional activity of the novel p53-isoform and concomitantly results in high levels of anti-apoptotic factors p21 and 14-3-3σ. Previous findings suggest that the biology of cancers with mutations at codon 273, which is one of the most common p53 alterations in various tumors, may be different than those with p53 mutations at other sites e.g. 175 or 258. In fact, the present results show that in "hotspot" 273 mutp53 tumor cells, where alternative splicing generates functional wtΔp53, severe genotoxic insult leads to the formation of polyploid giant cells. Therefore, it can be expected that in combination with wtΔp53 that is expressed in class II mutp53 cancer cells, radio- or chemotherapy could result in an uncoordinated cell cycle that is followed by polyploidization and clonogenic survival. From the above results it is apparent that the modulation of wtΔp53, e.g. the inhibition of its expression or activity, is of therapeutic interest, e.g. for the prevention of tumor progression. Moreover, the wtΔp53 molecule is an important target for screening, e.g. for diagnostic purposes.

The following Examples are intended to illustrate the invention.

Example 1

Materials and Methods (A) Cell Culture and γ-Irradiation

PRK cells (primary Rhesus monkey kidney cells) were prepared as described previously (von der Weth and Deppert, Virology 189 (1992), 334-339). The following cell lines were routinely grown according to the supplier's instructions: CV-1 (African green monkey epithelial kidney cell line; ATCC#CCL70), LLC-MK2 (Rhesus monkey kidney cell line; ATCC#CCL7), A431 (human epidermoid carcinoma; DSMZ#ACC91), SW480 (human colon carcinoma; DSMZ#ACC313), H1299 (human lung carcinoma; ATCC#CLR-5803), CCRF-CEM (human T cell lymphoma; ATCC#119-CCL), Karpas-299 (human T cell lymphoma; DSMZ#ACC31), and HL60 (human promyelocytic cell line; ATCC#CCL240). The HSC93 cell line (human B cell lymphoma) was grown as spinner culture in RPMI-1640, supplemented with 10% FCS and 2 mM glutamine at 37° C. Cells were γ-irradiated using a $^{137}$CS source with a dosage of 20 Gy. Hybridoma PAb101 specific against SV40 T-Ag(Gurney et al., J. Virol. 34 (1980), 752-763) was grown as spinner culture in RPMI-1640/DMEM (1:1) supplemented with 5% FCS and 4 mM glutamine at 37° C.

(B) Cell Cycle Analysis and Cell Viability

Fluorescence-activated cell sorting (FACS) was performed as described (Dehde et al., Mol. Cell. Biol. 7 (2001), 2581-2593). Harvested Cells were scored for viability by trypan blue exclusion.

(C) Immunological Reagents

The following primary antibodies were used: anti-p53 monoclonal antibodies DO1 (Oncogene, Boston, Mass.), DO12 and ICA9 (Serotec, Raleigh, N.C.); anti-p53 rabbit polyclonal antibody "SAPU" (S238-120; Scottish Antibody Production Unit, Lanarkshire, Scotland); anti-bax rabbit polyclonal antibody (Upstate Biotechnology, Lake Placid, N.Y.); anti-mdm2 monoclonal antibody SMP14 (BD PharMingen, San Diego, Calif.); anti-PIG3 rabbit polyclonal antibody (Ab-1; Oncogene); anti-p21 rabbit polyclonal antibody (H-164; Santa Cruz Biotechnology, Santa Cruz, Calif.); anti-14-3-3σ-goat polyclonal antibody (N-14; Santa Cruz); anti-14-3-3σ-rabbit polyclonal antibody (K-19; Santa Cruz); anti-FLAG monoclonal antibody (M2; SIGMA, Taufkirchen, Germany).

(D) Protein Manipulations

Immunoprecipitation and immunoblotting were performed as described previously (Dehde et al., 2001). For the detection of the p53-p53 oligomerization in H1299 cells, the complexes were resolved by SDS-PAGE on 10% polyacrylamide gels that were prepared with 30% acrylamide and 0.5% bis-acrylamide.

(E) Chromatin Immunoprecipitation Assay (ChIP)

ChIP was performed with $10^6$ cells per assay and according to the manufacturer's instruction (Upstate Biotechnology, cf. above). The following primers were used to determine the levels of p21-, 14-3-3σ-, mdm2-, bax- and PIG3-promoter respectively:

```
5'-AGAGTAACAGGCTAAGGCTTACCT-3'      (SEQ ID NO: 2)
and

5'-TGTGGCTCTGATTGGCTTTCTGGCCAT-3';  (SEQ ID NO: 3)

5'-GAGCTGTGATCATACCACTGTA-3'        (SEQ ID NO: 4)
and

5'-GGACATGTCTGTGCTAATGCT-3';        (SEQ ID NO: 5)

5'-AGCTTTTCCTCTTGAGCTGGTCA-3'       (SEQ ID NO: 6)
and

5'-TTCAATCGCCACTGAACACAGCT-3';      (SEQ ID NO: 7)

5'-TCACAAGTTAGACAAGCCTGGG-3'        (SEQ ID NO: 8)
and

5'-ACGTGACTGTCCAATGAGCATCT-3',      (SEQ ID NO: 9)

5'-CAGGACTGTCAGGAGGAGGCGAGTGATAA    (SEQ ID NO: 10)
GG-3'
and

5'-GTGCGATTCTAGCTCTCACTTCAAGGAGA    (SEQ ID NO: 11)
GG-3'.
```

(F) RT-PCR and Sequencing Analysis

Total RNA was isolated by the acid-guanidinium-phenol-chloroform method (Chomczynski and Sacchi, Anal. Biochem. 162 (1987), 156-159) from the cell lines as described above. Reverse transcription reactions were run with 1-2 μg of total RNA using the Superscript Preamplification System (Invitrogen Life Technologies, Groningen, the Netherlands) according to manufacturer's instructions. Reactions were performed with poly-dT and random hexamer primers for the cDNA synthesis. The cDNA was amplified in two rounds of PCR to detect alternative-spliced products. The following p53-specific primer sets were used in the first approach: primers E1F (5'-CCATGGAGGAGCCGCAGTCAG-3'(SEQ ID NO: 12)) and E7R (5'-CGCCCATGCAGGAACTGTTA-3' (SEQ ID NO: 13)) for the first round PCR and primers E1bF (5'-CAGTCAGATCCTAGCGTCGAG-3'(SEQ ID NO: 14)) and E7bR (5'-GGTGGTACAGTCAGAGCCAA-3'(SEQ ID NO: 15)) for the nested PCR. In the second approach the following primers were used: for the first round PCR the primers E4F (5'-CTCCTGGCCCCTGTCATCGT-3'(SEQ ID NO: 16)) and E11R (5'-GCTCAGTGGGGGAACAAGAAC-3'(SEQ ID NO: 17)) and for the nested PCR the primers E6/7F (5'-TGAGGTTGGCTCTGACTGTA-3'(SEQ ID NO: 18)) and E11bR (5'-AGAATGTCAGTCTGAGTCAGG-3'(SEQ ID NO: 19)). PCR products were loaded on a 1% agarose gel, bands were sliced from the gel, and DNA was purified with QIAEX II gel extraction kit (QIAGEN, Valencia, Calif.). All PCR and products were analyzed by direct sequencing with an automated ABI PRISM 377 DNA sequencer using the ABI PRISM dye-primer cycle sequencing chemistry.

(G) Cloning of Δp53cDNA, Plasmids and Transient Transfection

The 984-bp "wild-type" Δp53cDNA and the 984-bp mutant Δp53cDNA (mutation at codon 175) were generated by PCR with specific primers: p53F-Eco (5'-TATATGAAT-TCGGGATCCCATGGAGGAGCCGCAGTCAGA-3'(SEQ ID NO: 20)) and p53 R-Eco (5'-TATATGAATTCGGT-CAGTCTGAGTCAGGCCCTTCTGTCT-3'(SEQ ID NO: 21)) and cloned into the EcoRI site of pCDNA3 (Clontech, Palo Alto, Calif.). Mutp53-273H was excised from the pC53.273 plasmid with EcoRI and cloned into the EcoRI site of pCDNA3. For tagging the p53 proteins with the FLAG-tag, the p53 cDNAs were inserted into the BamHI/ApaI site of the mammalian expression vector pCMV-Tag2B (Stratagene, La Jolla, Calif.). Transient transfection experiments were performed with nucleofactor kit V according to the manufacturer's recommendations (amaxa biosystems, Cologne, Germany).

Example 2

RT-PCR Reveals a Novel p53 Splice Variant

A highly sensitive, non-quantitative nested reverse transcription (RT)-PCR-based approach (Cooley and Bergtrom, Arch. Biochem. Biophys. 390 (2001), 71-77) was used to detect possible alternative splicing of primate p53. The cDNA was amplified in two rounds of PCR to detect alternate-spliced p53 products. In the first approach, the region located between the N-terminus and the core-domain of p53 was amplified using the PCR primers E1F and E7R followed by a second-stage PCR reaction with primers E1bF and E7bR. Amplification of exons 1-7 generated the expected 693-bp PCR product, but no additional amplicon (data not shown). Sequence analysis confirmed that the transcript represents the regularly spliced p53. In the second approach, the region located between the core-domain and the very C-terminus of primate p53 was amplified. In the first stage of the two-stage PCR amplification, the cDNA was amplified between exon 4 and C-terminal exon 11 by using appropriate sense (E4F) and antisense (E11R) primers. The second-stage PCR reaction was performed with nested PCR primers to exon 6/7 (E6/7F) and exon E11 (E11bR). Amplification of exons 6/7-11 generated the expected 520-bp PCR product and one additional 325-bp amplicon (FIG. 1A). The two PCR products were detected in primary and established wtp53 human and monkey cells of different tissue types (FIG. 1A, lanes 1-5). In addition, both amplicons were found in mutp53 primate cells (FIG. 1A, lanes 6-8). Sequence analysis of both bands revealed that the major band (520 bp) represents the regularly spliced full-length p53, whereas the other lower molecular weight band (325 bp) results from alternative splicing (FIG. 1A). The alternative splice product designated as Δp53 lacks 198 nucleotides that are located in exons 7, 8 and 9 (FIG. 1B). The deletion junction contains a donor site-like splicing-cassette within the coding exon 7 (nucleotide 767) and an acceptor site-like splicing-cassette within the coding exon 9 (nucleotide 965) (FIG. 1C). The resulting Δp53 transcript that contains the unique junction of exon 7 with 9 does not alter the open reading frame. In addition, sequence analysis of the entire 984-bp transcript showed that no additional alterations of the Δp53 coding sequence exist. Thus, the novel p53-isoform lacks 66 amino acid residues, which are located in the central portion and the hinge region of the protein, but Δp53 has the functionally important C-terminal domain (FIG. 1D).

Further investigation showed that the existence of the donor site-like splicing-cassette and an acceptor site-like splicing-cassette is required to generate Δp53. In mouse, rat, hamster and guinea pig, where the splicing cassettes are not conserved, the novel p53-isoform is not generated as evidenced by RT-PCR analysis (data not shown).

Example 3

Δp53 is Detectable at the Protein Level and Forms Homo- but Not Hetero-Oligomers It was investigated whether the alternative splice product of p53 is detectable at the protein level. Wtp53 containing primary rhesus kidney cells (PRK) and the wtp53 expressing human cell line HSC93 were γ-irradiated and analyzed by immunoblotting with anti-p53 monoclonal antibodies. The N-terminal specific antibody DO1 (residues 21-25) and the C-terminal specific antibody ICA9 (residues 388-393) were used to probe for full-length p53 and Δp53. Following irradiation, both forms of p53 were detected with the N- and C-terminal specific antibodies (FIG. 2A, lanes 2 and 4) indicating that the faster migrating form of p53 is not the product of proteolytic degradation. In non-irradiated mutp53 cells, full-length p53 and Δp53 are expressed at high levels and readily detectable with anti-p53 antibodies DO1 and ICA9 (FIG. 2A, lanes 5-10). However, Δp53 was not recognized by antibody DO12 specific for residues 256-270 that are deleted in Δp53 (data not shown). Therefore, antibody DO12 recognizes only full-length p53.

Since the tetramerization domain is preserved in Δp53, it was investigated whether the p53-isoform has retained the ability to form complexes with full-length p53 or Δp53. Complex formation of endogenous Δp53 with full-length p53 was evaluated in primate cells with antibody DO12 specific for full-length p53. Immunoblot analysis of DO12-precipitated full-length p53 demonstrated that Δp53 was not co-precipitated and, therefore, does not bind to full-length wtp53 (FIG. 2B, lanes 1-4) or mutp53 (lanes 5-10). The ability of Δp53 to interact with itself was investigated by cloning the "wild-type"-Δp53 (wtΔp53) and "mutant"-Δp53-175 (mutΔp53, mutation at codon 175) cDNA into the mammalian expression vector pCDNA3 and the FLAG-tag containing vector pCMV-Tag2B. Control experiments were carried out with pCDNA3 and pCMV-Tag2B constructs expressing untagged and FLAG-tagged full-length wtp53 and mutp53. The p53$^{-/-}$ human cell line H1299 was transfected with both constructs and the monoclonal anti-FLAG antibody M2 was used for the coimmunoprecipitation experiments. Oligomerization of immunoprecipitated FLAG-p53 with untagged p53 was analyzed by Western blot with polyclonal anti-p53 antibody "SAPU." As expected, full-length p53 formed complexes with itself but not with Δp53 (FIG. 2C, lanes 1-3 and 5-7). In contrast, the coimmunoprecipitation experiments showed that Δp53 was able to form complexes with itself (FIG. 2C, lanes 8 and 9). Thus, Δp53 forms homo- but not hetero-oligomers indicating that Δp53 function could be independent of full-length p53.

Example 4

Δp53 Displays Differential Transcriptional Activity

The novel p53-isoform was analyzed for the ability to transactivate endogenous p53-inducible promoters in p53$^{-/-}$ H1299 cells. After transient transfection of pCDNA3-Δp53, the expression of the p53-isoform was confirmed by immunoblotting (FIG. 3A, lane 4). Expression of Δp53 in H1299 cells resulted in transactivation of the endogenous p21- and 14-3-3σ- but not the mdm2-, bax- and PIG3-promoters (FIG. 3B, lanes 2). Control experiments were carried out with pCDNA3 constructs expressing full-length wtp53 and mutp53-273H (FIG. 3A, lanes 3 and 5).

As expected, full-length wtp53 transactivated all of the investigated endogenous promoters, whereas full-length mutp53-273H was impaired for promoter activation (FIG. 3B, lanes 1 and 3). In addition, co-transfection experiments with the appropriate luciferase reporter constructs were carried out to confirm the selective promoter activation of Δp53. In H1299 cells, which were transiently transfected with the Δp53 plasmid, only transactivation of the p21- and 14-3-3σ- but not the mdm2-, bax- and PIG3-luciferase reporter constructs was observed (data not shown).

The observed differential transcriptional activity of Δp53 was studied in more detail. Wtp53 expressing CV-1 cells were γ-irradiated and chromatin-immunoprecipitation (ChIP) was performed to detect association of Δp53 with the endogenous p21-, 14-3-3σ-, mdm2-, bax- and PIG3-promoters. Following irradiation, cross-linked p53-DNA complexes were immunoprecipitated with the C- and N-terminal specific anti-p53 antibodies DO1 and ICA9 respectively to recover full-length p53 and Δp53. Additionally, core-specific antibody DO12 was used to immunoprecipitate full-length p53 exclusively. The non-p53 specific monoclonal antibody PAb101 served as negative control. Immunoprecipitates were analyzed for the presence of full-length p53 and Δp53 with polyclonal anti-p53 antibody "SAPU" by Western blot (FIG. 4A). The presence of p53-associated p21-, 14-3-3σ, mdm2-, bax- and PIG3-promoter DNA was determined by PCR amplification with specific primers. In γ-irradiated wtp53 CV-1 cells, binding of p53 to the endogenous p21-, 14-3-3σ, mdm2-, bax- and PIG3-promoter was detected with all three applied anti-p53 antibodies (FIG. 4B), indicating that full-length wtp53 associated with all utilized promoters. Thus, in irradiated wtp53 cells, it is not possible to discriminate between promoter bound full-length wtp53 and Δp53. Since Δp53 is not complexed to full-length p53 (FIG. 2B, C), the physiological implication of Δp53 in the mutp53 cell line A431 (mutation at codon 273) was investigated, where alternative splicing generates wtΔp53 that lacks the inactivating mutation. Following irradiation, cross-linked p53-DNA complexes were immunoprecipitated with the epitope specific anti-p53 antibodies and analyzed as described above (FIG. 4C). The ChIP-PCR results demonstrate that in the DNA damaged mutp53 cell line A431, wtΔp53 but not full-length mutp53-273 was bound to the p21- and 14-3-3σ-promoter (FIG. 4D). However, no interaction was observed with the mdm2-, bax- and PIG3-promoter, confirming that promoter binding of wtΔp53 is selective (FIG. 4D). ChIP-PCR performed with the wtΔp53 expressing mutp53 cell lines SW480 (mutation at codon 273 and 309) and Karpas-299 (mutation at codon 273) confirmed the selective promoter binding of wtΔp53 (data not shown). The p53-isoform is constitutively expressed in mutp53 cells and accumulates to significant levels (FIG. 2A, lanes 5-10). It was investigated whether wtΔp53 requires activation for efficient promoter DNA binding. In the non-irradiated mutp53-273 cell lines A431, SW480 and Karpas-299 wtΔp53 associated promoters were not observed, pointing out that genotoxic stress is required to enable promoter binding of wtΔp53 (data not shown). In addition, another class of mutp53 cell lines was used for ChIP-PCR. In those cell lines, the p53 gene contains a mutation that is not removed by alternative splicing and therefore expresses mutΔp53. In the mutp53 cell line LLC-MK2 (codons 237-239 are deleted), full-length p53 and mutΔp53 associated promoters were not detected by ChIP-PCR, independent of genotoxic stress (FIGS. 4E and F). The same results were obtained with the mutΔp53 expressing mutp53 cell lines CA46 (mutation at codon 248) and CEM (mutations at codons 175 and 248) (data not shown).

Then, it was investigated whether binding of endogenous wtΔp53 to the endogenous p21- and 14-3-3σ-promoter leads to their transactivation. In the control experiment, which was performed with the wtp53 expressing cell line CV-1, upregulation of p21, 14-3-3σ, mdm2, bax and PIG3 was observed at the indicated time points after γ-irradiation (FIGS. 5A and B, left panels). In contrast, induction of these p53-inducible factors was not observed in stress-induced mutΔp53 expressing mutp53 LLC-MK2 cells (FIGS. 5A and B, right panels). However, upon γ-irradiation upregulation of the anti-apoptotic factors p21 and 14-3-3σ was detected in the wtΔp53 expressing mutp53 cell line A431 (FIGS. 5A and B, middle panels). The results demonstrate that in wtΔp53 expressing mutp53 cells, genotoxic stress leads to Δp53-dependent transactivation of the p21- and 14-3-3σ-promoter, but Δp53 does not induce genes like mdm2, bax and PIG3.

Example 5

Δp53 Induces Polyploidization in Irradiated mutp53-273 Cells

To study the biological effects of the expression of Δp53 in the presence of mutp53, the response of wtp53 (HSC93), p53$^{-/-}$ (HL60), mutΔp53 expressing mutp53 (CEM) and wtΔp53 expressing mutp53-273 (Karpas-299, A431) cells to irradiation was studied. Cells were scored for viability at the indicated time points after irradiation and analyzed by flow cytometry. The wtp53, the p53$^{-/-}$ and the mutΔp53 expressing mutp53 cells died significantly sooner than the wtΔp53 expressing mutp53-273 cells as evidenced by trypan blue exclusion (FIG. 6A) and by an increase in the sub-G1 DNA content starting at 24 h post irradiation (FIG. 6B). In contrast, the wtΔp53 expressing mutp53-273 Karpas-299 and A431 cells, which express p53-induced anti-apoptotic but not pro-apoptotic proteins upon irradiation, maintained a cell cycle arrest with a 4N DNA content (FIG. 6B). Furthermore, a significant difference became apparent 24-h post irradiation. While DNA damaged wtp53, p53$^{-/-}$ and mutp53 cells died, many wtΔp53 expressing mutp53-273 Karpas-299 and A431 cells entered into a DNA synthesis phase, resulting in a significant population of cells with a DNA content of 8N (FIG. 6B). Polyploidization was also observed after irradiation of wtΔp53 expressing mutp53-273 cell line SW480 (data not shown). The results indicate that in the absence of the pro-apoptotic factors bax and PIG3, expression of p21 and 14-3-

3σ counteracts apoptosis and promotes endoreduplication in DNA damaged wtΔp53 expressing mutp53-273 tumor cells.

Example 6

Δp53 Maintains the ATR-Intra-S Phase Checkpoint to Promote Coordinated Repair and Replication The physiological consequences of the Δp53-mediated S phase attenuation were analyzed in more detail. Hence, DNA repair and replication events were monitored in G1/S-UV-irradiated wtp53 CV-1 and TO-CV-1 cells. First, the kinetics of undisturbed DNA replication was determined in all cell lines. As expected, in all mock-treated cell lines, $^3$H incorporation into DNA increased immediately and ceased 8 hr later, indicating that DNA replication was complete as shown in FIG. 8A. However, in irradiated wtp53 CV-1 and TO-CV-1 null cells, DNA replication was blocked for the first 2 hr and incorporation of $^3$H into DNA remained low for additional 4 hr (FIG. 8B, top). Six hours after irradiation, the replication activity increased suddenly and ceased 6 hr later, indicating that the duration of the replicative S phase, which is normally 8 hr, was prolonged for 4 hr (FIG. 8B, top). In contrast, in irradiated Flag-mutΔp53-expressing cells, $^3$H incorporation into DNA was only delayed for 2 hr and replication activity ceased 8 hr after the G1/S transition (FIG. 8B, middle). Thus, the overall replication time was not prolonged in mutΔp53 cells. In contrast, in wtp53 TO-CV-1-Flag-mutp53 cells, which have inactivated endogenous wtp53 but functional Δp53, S phase was prolonged from 8 hr to 12 hr (FIG. 8B, bottom). Taken together, data show that Δp53/p53-independent downregulation of cyclin E-Cdk2 activity inhibits DNA replication only for 2 hr. However, inhibition of DNA replication for additional 4 hr depends on Δp53-mediated reduction of cyclin A-Cdk activity via p21.

The observed delayed onset of rapid DNA replication for 6 hr in wtΔp53 cells suggested that the additional time might be used for repair. Therefore, DNA repair activity was examined by monitoring the decrease of relative amounts of DNA damage applying the alkaline comet assay. The assay measures single-strand (ssDNA) DNA breakage that is generated by nucleotide excision repair. Following mock or UV-irradiation at the G1/S transition, ssDNA breakage was assessed at the indicated time points. In mock-treated cells, the median tail moments demonstrate that the ssDNA signal, which derives mainly from the 40 nucleotide long RNA-DNA primers that are generated by DNA polymerase α-primase during the initiation and elongation replication process, correlates with the graph obtained from $^3$H incorporation (FIG. 8A). Thus, in mock-treated cells, the ssDNA signal reflects DNA replication activity. In contrast, in irradiated wtp53 CV-1 and TO-CV-1 null cells, the median tail moments show that the ssDNA signal peaks at 1 and 8 hpi (FIG. 8B, top). Data indicate that the first ssDNA signal is generated by repair activity, whereas the second one derives from replication priming events since the second ssDNA signal matches the kinetics of DNA synthesis (FIG. 8B, top). In irradiated wtp53 TO-CV-1-Flag-mutΔp53 cells, the kinetics of the ssDNA signal also shows two activity peaks (FIG. 8B, middle). However, the second ssDNA signal has its maximum 10 hpi, occurs during G2 attenuation, and does not match the kinetics of DNA replication. Thus, in cells devoid of functional Δp53, the first ssDNA signal derives from simultaneous DNA repair and replication activities, whereas the second one reflects repair activity subsequent to activation of the G2 checkpoint. Finally, irradiation of Flag-mutp53-expressing cells demonstrated that wtp53 is not required to promote uncoupling of repair and replication events (FIG. 8B, bottom).

The UV-induced ATR signaling pathway causes transient delays in S phase progression and reversible inhibition of DNA replication for several hours. However, the previously elucidated ATR-Chk1-Cdc25A-cyclin E-Cdk2 pathway inhibits replication only for a short time. Thus, this event could not account for the 6 hr ongoing inhibition of DNA replication, indicating the existence of an additional pathway. It is shown that the key player of this pathway, which allows extended S phase attenuation and inhibition of replication is Δp53; its transcriptional activity leads to p21-mediated down-regulation of cyclin A-Cdk2 activity, an activity that is required for S phase progression and DNA synthesis. Therefore, at least two parallel branches of the intra-S phase checkpoint cooperate to slow down S phase progression and to prevent origin firing, both of which are controlled by the ATR signaling pathway. The Cdc25A-cyclin E-Cdk2 pathway is executed rapidly, independently of p53 and Δp53, but prevents origin firing only for 2 hr. The other slower-operating branch, which depends on the Δp53-p21-cyclin A-Cdk2 pathway, inhibits DNA replication for additional 4 hr. Apart from the inhibition of replication, the ATR-Δp53-p21-cyclin A-Cdk2 pathway provides another critical function: the repair of damaged DNA before DNA is duplicated. The importance of Δp53 for the ATR-intra-S phase checkpoint was demonstrated by the fact that inactivation of endogenous wtΔp53 prevented downregulation of cyclin A-Cdk2 activity, resulting in coupled repair and replication events. Moreover, cells deficient in Δp53 accumulated DNA damage that derived from inappropriately repaired DNA due to simultaneous repair and replication events as indicated by subsequent repair activity during attenuated G2 progression. Although the G2 checkpoint should capture any cells that have exited S phase with damaged DNA, these cells may have already missed their best opportunity to perform error-free repair. Thus, the ATR-intra-S phase checkpoint, through the combined action of the Chk1-Cdc25A-cyclin E-Cdk2 and the Δp53-p21-cyclin A-Cdk2 pathways, allows repair of the damaged DNA before replication is initiated in order to ensure genetic integrity of the replicated DNA.

In summary, data suggest that the UV-induced ATR-intra-S phase checkpoint consists of two distinct components that cooperate to uncouple repair and replication events. With the first one, the 2 hr initiation phase is Δp53/p53 independent and with the second one, the 4 hr maintenance phase depends on the transcriptional activity of Δp53.

Example 7

Δp53 Attenuates S Phase Progression Via Downregulation of Cyclin A-Cdk Activity

Entry and progression through S phase requires the activities of cyclin E- and cyclin A-Cdk2, respectively, whereas cyclin A-Cdk1 is required for S/G2 transition and G2 progression. Thus, subsequent to G1/S-UV irradiation the observed S phase attenuation was most likely caused by downregulation of those activities. In all cell lines tested, cyclin E-Cdk2 activity dropped immediately due to degradation of the kinase-activating phosphatase Cdc25A and was restored as soon as Cdc25A became stable again (FIG. 9A,). Thus, the Cdc25A-mediated inhibition of cyclin E-Cdk2 activity is executed rapidly, independently of Δp53/p53, but delays S phase progression only for 2 hr.

In mock-treated cells, the cyclin A-Cdk activity increased steadily after G1/S transition and declined 12 hr later, indicating that cells had progressed through S and G2 and were entering mitosis (FIG. 9C). However, after irradiating wtp53 TO-CV-1 null and CV-1 cells, the Cdk activity was substantially downregulated for 8 hr, followed by a moderate but steady increase (FIG. 9C). In irradiated, Flag-mutΔp53-expressing cells, cyclin A-Cdk activity increased steadily despite a slight delay due to the short Cdc25A-mediated cyclin E-Cdk2 inhibition (FIG. 9C). However, 10 hpi, the kinase activity dropped suddenly and prolonged reduction was observed for the next 5 hr (FIG. 9C), confirming that progression through G2 was delayed. In contrast, irradiated wtp53 TO-CV-1-Flag-mutp53 cells, deficient in functional wtp53, displayed like wtp53 TO-CV-1 null cells significant reduction of cyclin A-Cdk activity for the first 8 hpi (FIG. 9C), resulting in delayed S phase progression. However, 8 hpi, the decrease in kinase activity was notably lower than in wtp53 TO-CV-1 null cells. Thus, results show that significant reduction in cyclin A-Cdk activity during the first 8 hr correlates with functional wtΔp53, whereas downregulation of this Cdk activity starting at 8 hpi correlates with functional wtp53.

Downregulation of cyclin A-Cdk activity can be facilitated by interaction with p21, thus formation of the protein complex was evaluated subsequent to G1/S-UV irradiation. First, the association of cyclin A with Cdk2 and Cdk1 during S and G2 phase progression was monitored in G1/S mock-treated wtp53 TO-CV-1 null cells. The level of cyclin A increased during S and G2 progression (10 hr) and declined when cells entered mitosis (12 hr; FIG. 9D, panel 1). Soon after cells crossed G1/S, cyclin A was increasingly associated with Cdk2 during S and S/G2 (0-8 hr), whereas S/G2 and G2 promoting Cdk1 associated with cyclin A shortly before the cells completed the replicative stage (6 hr; FIG. 9D, panel 1). As expected, in mock-treated cells, the kinase was not associated with p21 (FIG. 9D, panel 1). Thus, the formation of the cyclin A-Cdk2/1 complexes correlates with the activity of the cyclin A-dependent kinases and reflects undisturbed S and G2 progression as confirmed by FACS. Conversely, in irradiated wtp53 TO-CV-1 null cells, complex formation of cyclin A with Cdk2 was extended until 16 hpi, and interaction with G2-promoting factor Cdk1 was postponed for 2 hr (FIG. 9D, panel 2), indicating that entry into G2 was delayed. Western blot analysis of immunoprecipitated cyclin A-Cdk demonstrated association with p21 from 2-16 hpi (FIG. 9D, panel 2) and correlated with reduced kinase activity (FIG. 9C). In irradiated Flag-mutΔp53-expressing cells, complex formation of cyclin A with Cdk2 and Cdk1 (FIG. 9D, panel 3) was identical with the one observed in irradiated wtp53 TO-CV-1 null cells (FIG. 9D, panel 2). However, in those cells, cyclin A-Cdk-p21 complexes were not detected until 8 hpi due to abrogation of Δp53-dependent p21 induction (FIG. 9D, panel 3). The finding correlated with the observation that the kinase activity was not substantially reduced during the first 8 hpi (FIG. 9C), resulting in steady S phase progression. However, starting 8 hpi, cyclin A-Cdk associated with wtp53-transactivated p21 until 16 hpi and correlated with the observed reduced kinase activity (FIG. 9C).

In contrast, in Flag-mutp53-expressing cells, p21 associated with cyclin A-Cdk until 8 hpi (FIG. 9D, panel 4), demonstrating that during the first 8 hpi induction of p21 depends solely on Δp53. Consequently, downregulation of the Cdk activity was observed (FIG. 9C), most likely cyclin A-Cdk2, since cyclin A-Cdk1 complexes were not detectable until 8 hpi (FIG. 9D, panels 2 and 3). Moreover, starting 10 hpi, lack of functional wtp53 generated p21-free cyclin A-Cdk complexes and explains why the kinase activity increased earlier in wtp53 TO-CV-1-Flag-mutp53 than in null cells (FIG. 9C). However, untimely increase in cyclin A-Cdk activity presumably cyclin A-Cdk1 had no negative impact on Δp53-mediated S phase attenuation and further cell cycle progression.

Taken together, data imply that subsequent to irradiation at the G1/S transition Δp53 reduces the activity of S phase-specific cyclin A-Cdk2 and thus is responsible for S phase attenuation, whereas p53 downregulates the activity of S/G2- and G2-specific cyclin A-Cdk1. However, p53-mediated reduction of cyclin A-Cdk1 activity is dispensable for S phase attenuation and thus not essential for the ATR-intra-S phase checkpoint.

Example 8

Transcriptional Activity of Δp53 and p53 is Activated and Inactivated Consecutively The observed cell cycle specific p21-promoter binding of Δp53 and p53 suggests that both p53 forms exert their transcriptional activity independent from each other. Thus, p21 induction was monitored in Dox induced, G1/S-irradiated wtp53 TO-CV-1 cells till 20 h post irradiation (hpi). Western blot analysis revealed that in the control cell line wtp53 TO-CV-1-null, where dominant-negative effects do not impair endogenous wtp53 and wtΔp53, the p21 level was increased between 2 and 16 hpi (FIG. 10A, top). In cells expressing Flag-mutΔp53 p21 was elevated between 8 and 16 hpi (FIG. 10A, middle), whereas in cells expressing Flag-mutp53 p21 upregulation was observed between 2 and 10 hpi (bottom). Thus, during the first 10 hpi, p21 induction is mediated by Δp53, whereas p53 is responsible for p21 upregulation starting 8 hpi.

The observation that p21 is initially transactivated by Δp53 and at a later time point by p53 was further investigated by performing ChIP-PCR at 3 and 9 h post G1/S-irradiation. Cross-linked Δp53/p53-DNA complexes were precipitated with anti-p53 DO1, anti-fl p53 DO12 and anti-Flag M2 antibodies; anti-T-Ag antibody PAb101 served as negative control. Data show that in wtp53 TO-CV-1-null cells, p21-promoter DNA was associated only with the DO1 precipitate 3 hpi, whereas 9 hpi p21-promoter DNA was also recovered from the DO12 precipitate (FIG. 10B, left panels). Cross-linked Δp53/p53-DNA complexes obtained from wtp53 TO-CV-1-Flag-wtΔp53 and -wtp53 cells showed that 3 hpi only Flag-wtΔp53 was associated with p21-promoter DNA, whereas Flag-wtp53 bound the p21-promoter DNA 9 hpi (FIG. 10B, middle and right panels). Experiments performed with cells expressing Flag-mutΔp53 or -mutp53 showed that Flag-mutΔp53 caused abrogation of endogenous wtΔp53 p21-promoter binding 3 hpi (FIG. 10C, middle panels), whereas Flag-mutp53 prevented p21-promoter binding of endogenous wtp53 9 hpi (right panels). Accordingly, the results demonstrate that the transcriptional activity of Δp53 and p53 is activated and inactivated consecutively and hence strictly separated.

Example 9

Δp53 is Transcriptionally Active Only in Irradiated S Phase Cells

Since Δp53 does not transactivate apoptosis-promoting genes, it was hypothesized that Δp53 functions in damaged S phase cells. The assumption was first investigated by analyzing the protein and mRNA level of p21 in wtp53 CV-1 cells that were irradiated in G1, early S, and G2. In order to investigate which p53 form is responsible for p21 induction, association of p53 and Δp53 with the p21 promoter was examined by ChIP-PCR. p21 promoter binding of p53 was detected in G1 and G2, but not in S, since p21 promoter DNA was not obtained with anti-fl p53 antibody DO12 (FIG. 11A). However, recovery of p21 promoter DNA from DO1 and ICA9 precipitates points to Δp53-mediated p21 transactivation in S phase (FIG. 11A).

In view of the fact that Δp53-specific antibodies are not at hand to allow direct discrimination between p53 and Δp53, wtp53 CV-1 cells were chosen to establish an inducible cell system that expresses the appropriate Flag-tagged wt or mutΔp53/p53 protein or empty vector (null) upon Dox addition. Inducible Flag-tagged protein expression in the respective wtp53 TO-CV-1 cell line was analyzed by Western blot (FIG. 11B). Additionally, inactivation of endogenous wtp53 or wtΔp53, accomplished by complex formation with the corresponding ectopically expressed Flag-tagged mutp53/Δp53, allows studying the physiological impact of endogenous wtp53 and wtΔp53 individually in an isogenic cell system. Probing the anti-Flag precipitates with anti-Flag M2 (FIG. 11C, top), anti-fl p53 DO12 (middle), and anti-p53 DO1 (bottom) antibodies showed that Flag-wtp53 and -mutp53 interacted with endogenous wtp53, but not with endogenous wtΔp53 (FIG. 11C, lanes 1 and 2); precipitated Flag-wtΔp53 and -mutΔp53 oligomerized with endogenous wtΔp53, but not with endogenous wtp53 (FIG. 11C, lanes 3 and 4). As expected, anti-fl p53 antibody DO12 did not recognize Flag-wtΔp53, -mutΔp53, or endogenous wtΔp53 (FIG. 11C, middle, lanes 3 and 4). ChIP-PCR demonstrated that ectopic Flag-mutp53 abrogated p21 promoter binding of endogenous wtp53 (FIG. 11D, panel 1), whereas Flag-mutΔp53 prevented promoter binding of endogenous wtΔp53 (FIG. 11D, panel 2).

The inducible wtp53 TO-CV-1-Flag cell system was used to confirm that p21 promoter association of p53 and Δp53 is cell cycle specific. Following UV irradiation in G1, early S, and G2, crosslinked Flag-Δp53/p53-DNA complexes were precipitated with anti-Flag antibody M2. Anti-fl p53 antibody DO12 and anti-T-Ag antibody PAb101 were used for the control experiments. Results show that in Flag-wtp53-expressing cells, p21 promoter DNA was recovered from anti-Flag and anti-fl p53 DO12 precipitates in G1 and G2, but not in S (FIG. 11D, panel 3). However, ChIP-PCR performed with Flag-wtΔp53-expressing cells demonstrates that only the anti-Flag precipitate derived from S phase contained $p^{21}$ promoter DNA, whereas p21 promoter DNA was recovered from G1 and G2 only with anti-fl p53 antibody DO12 (FIG. 11D, panel 4). Thus, data confirm that $p^{21}$ promoter binding of Δp53 is S phase specific, whereas p53 binds the p21 promoter exclusively in G1 and G2.

---

That which is claimed is:

1. A purified antibody which binds to a p53 variant polypeptide but not a wild-type p53 polypeptide, wherein the p53 variant polypeptide is encoded by a nucleic acid having a deletion junction that is SEQ ID NO. 25, wherein the purified antibody binds to an epitope comprising an amino acid sequence encoded by the deletion junction, wherein said variant polypeptide is characterized in that it is capable of transactivating the p21- and 14-3-3σ-promoter but not the mdm2-, bax- and PIG3-promoter.

2. A purified antibody which binds to a p53 variant polypeptide but not a wild-type p53 polypeptide, wherein the p53 variant polypeptide comprises the amino acid sequence of SEQ ID NO:24, wherein the purified antibody binds to an epitope comprising amino acids 256 to 258 of SEQ ID NO:24, and is capable of transactivating the p21- and 14-3-3σ-promoter but not the mdm2-, bax- and PIG3-promoter.

3. The purified antibody of claim 1, wherein the antibody is monoclonal.

4. The purified antibody of claim 2, wherein the antibody is monoclonal.

5. The purified antibody of claim 1, wherein the antibody is bound to a solid support.

6. The purified antibody of claim 2, wherein the antibody is bound to a solid support.

7. The purified antibody of claim 1, wherein the antibody is labeled with an enzyme, fluorescent compound, luminescent compound, ferromagnetic compound or a radioactive isotope.

8. The purified antibody of claim 2, wherein the antibody is labeled with an enzyme, fluorescent compound, luminescent compound, ferromagnetic compound or a radioactive isotope.

9. The purified antibody of claim 1 wherein the nucleic acid sequence that encodes for the p53 variant comprises the nucleic acid sequence of SEQ ID NO. 26.

* * * * *